(12) United States Patent
Elmaanaoui

(10) Patent No.: US 11,920,929 B2
(45) Date of Patent: Mar. 5, 2024

(54) DETECTING AND GUIDING OPTICAL CONNECTION(S) FOR ONE OR MORE IMAGING MODALITIES, SUCH AS IN OPTICAL COHERENCE TOMOGRAPHY

(71) Applicant: Canon U.S.A., Inc., Melville, NY (US)

(72) Inventor: Badr Elmaanaoui, Belmont, MA (US)

(73) Assignee: Canon U.S.A., Inc., Melville, NY (US)

( * ) Notice: Subject to any disclaimer, the term of this patent is extended or adjusted under 35 U.S.C. 154(b) by 144 days.

(21) Appl. No.: 17/354,241

(22) Filed: Jun. 22, 2021

(65) Prior Publication Data

US 2022/0042783 A1 Feb. 10, 2022

Related U.S. Application Data

(60) Provisional application No. 63/062,099, filed on Aug. 6, 2020.

(51) Int. Cl.
*G01B 9/02* (2022.01)
*A61B 1/00* (2006.01)
*G01B 9/02091* (2022.01)
*G06T 7/33* (2017.01)

(52) U.S. Cl.
CPC ...... *G01B 9/02091* (2013.01); *A61B 1/00163* (2013.01); *G06T 7/33* (2017.01); *G06T 2207/10101* (2013.01)

(58) Field of Classification Search
CPC .............. G01B 9/02091; G01B 9/0205; G01B 9/02068; G06T 7/33; G06T 2207/10101; A61B 1/00163; A61B 5/0066; A61B 5/0084
See application file for complete search history.

(56) References Cited

U.S. PATENT DOCUMENTS

| 7,132,645 | B2 | 11/2006 | Korn |
| 7,872,759 | B2 | 1/2011 | Tearney et al. |
| 7,889,348 | B2 | 2/2011 | Tearney et al. |
| 8,289,522 | B2 | 10/2012 | Tearney et al. |
| 8,928,889 | B2 | 1/2015 | Tearney et al. |
| 9,332,942 | B2 | 5/2016 | Jaffer et al. |
| 9,414,812 | B2 | 8/2016 | Elbert |

(Continued)

*Primary Examiner* — Uzma Alam
*Assistant Examiner* — Jonathon Cook
(74) *Attorney, Agent, or Firm* — Canon U.S.A., Inc. I.P. Division

(57) ABSTRACT

One or more devices, systems, methods, and storage mediums for detecting and guiding optical connection(s) using one or more imaging modalities are provided herein. Examples of applications include imaging, evaluating and diagnosing biological objects, such as, but not limited to, for Gastro-intestinal, cardio and/or ophthalmic applications, and being obtained via one or more optical instruments, such as, but not limited to, optical probes, catheters, capsules and needles (e.g., a biopsy needle). Devices, systems, methods, and storage mediums may include or involve a method, such as, but not limited to, for guiding and/or determining status of engagement and/or disengagement of one or more optical connections. A device, system, method, or storage medium may detect, monitor, and/or guide a probe/catheter to minimize, reduce, and/or avoid engagement and disengagement failures and to have a robust means of determining status of probe/catheter engagement to an apparatus or system.

16 Claims, 20 Drawing Sheets

(56) References Cited

U.S. PATENT DOCUMENTS

| | | | |
|---|---|---|---|
| 2009/0073455 A1* | 3/2009 | Onimura | A61B 5/6852 |
| | | | 356/479 |
| 2010/0092389 A1 | 4/2010 | Jaffer | |
| 2012/0101374 A1 | 4/2012 | Tearney et al. | |
| 2016/0228097 A1 | 8/2016 | Jaffer et al. | |
| 2018/0003481 A1 | 1/2018 | Yamada et al. | |
| 2018/0045501 A1* | 2/2018 | Elmaanaoui | |
| 2018/0271477 A1* | 9/2018 | Horiike | A61B 5/0035 |
| 2019/0374109 A1 | 12/2019 | Wu et al. | |
| 2020/0085285 A1* | 3/2020 | Yamada | A61B 1/00057 |
| 2021/0077037 A1 | 3/2021 | Kunio | |
| 2021/0174125 A1 | 6/2021 | Zhang | |

* cited by examiner

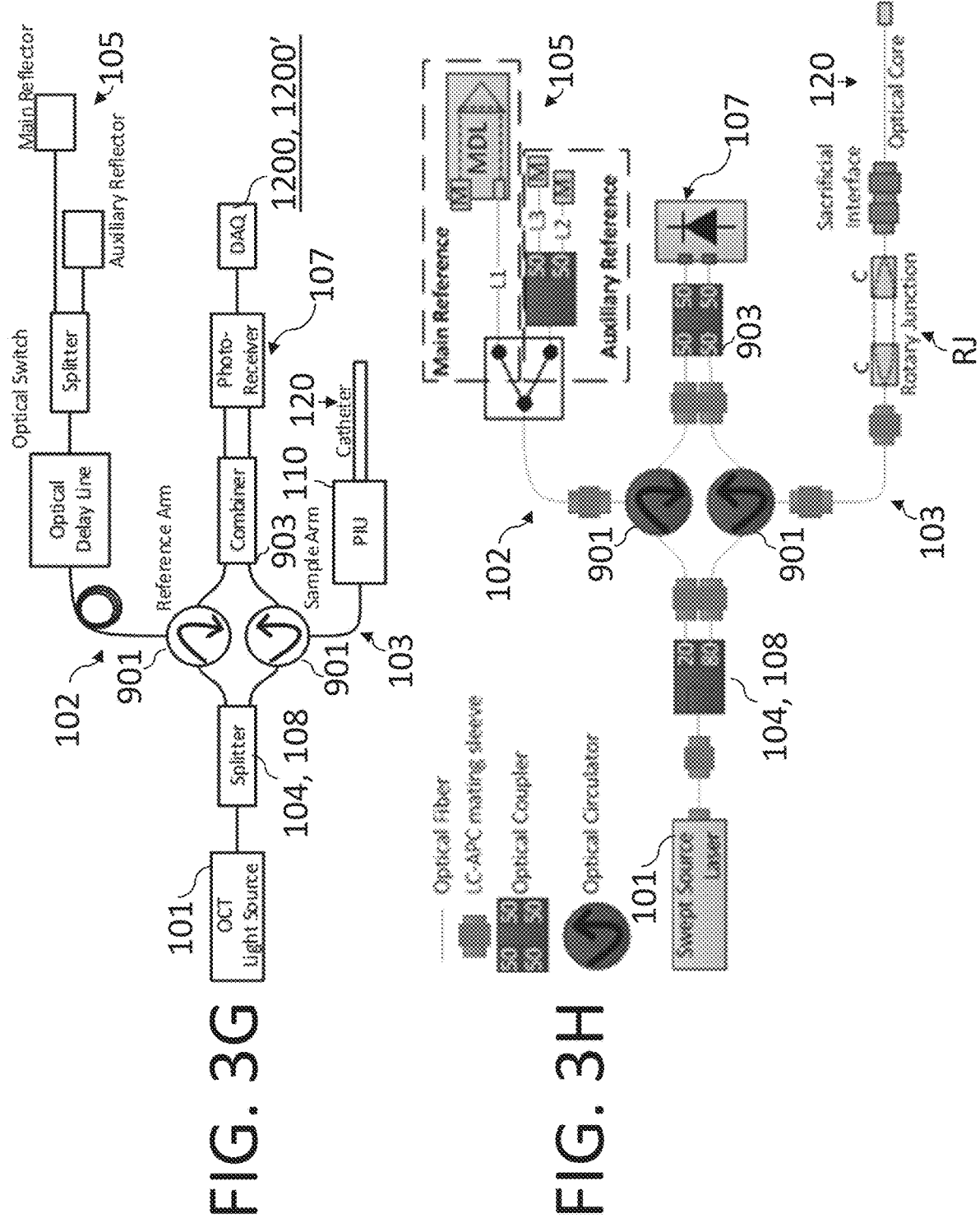

DETECTING AND GUIDING OPTICAL CONNECTION(S) FOR ONE OR MORE IMAGING MODALITIES, SUCH AS IN OPTICAL COHERENCE TOMOGRAPHY

CROSS-REFERENCE TO RELATED APPLICATION(S)

This application relates, and claims priority, to U.S. Patent Application Ser. No. 63/062,099, filed Aug. 6, 2020, the entire disclosure of which is incorporated by reference herein in its entirety.

FIELD OF THE DISCLOSURE

The present disclosure relates generally to the field of imaging and more particularly to one or more optical apparatuses, systems, methods (for using and/or manufacturing) and storage mediums, such as, but not limited to, fiber optic catheters, endoscopes and/or optical coherence tomography (OCT) and/or fluorescence apparatuses and systems, and methods and storage mediums, for use with same, to detect, monitor, and/or guide mating of a probe/catheter to such apparatuses, systems, and/or storage mediums, etc. when obtaining image(s) for one or more imaging modalities, such as OCT or other (e.g., intravascular ultrasound (IVUS), other lumen image(s), etc.). Examples of such applications include imaging, evaluating and diagnosing biological objects, such as, but not limited to, gastrointestinal, pulmonary, cardio, ophthalmic, and/or intravascular applications, and being obtained via one or more optical instruments, such as, but not limited to, one or more optical probes, one or more catheters, one or more endoscopes, one or more phase shift units (e.g., galvanometer scanner), one or more tethered capsules, one or more needles (e.g., a biopsy needle), and one or more bench top systems.

BACKGROUND

Fiber optic catheters and endoscopes have been developed to access to internal organs. For example in cardiology, OCT has been developed to see depth resolved images of vessels with a catheter. The catheter, which may include a sheath, a coil and an optical probe, may be navigated to a coronary artery.

Optical coherence tomography (OCT) is a technique for obtaining high-resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are. Single mode fibers may be used for OCT optical probes, and double clad fibers may be used for fluorescence and/or spectroscopy.

Percutaneous coronary intervention (PCI), and other vascular diagnosis and intervention procedures, have improved with the introduction of intravascular imaging (IVI) modalities, such as, but not limited to, intravascular ultrasound (IVUS) and optical coherence tomography (OCT). IVI modalities provide cross-sectional imaging of coronary arteries with precise lesion information (e.g., lumen size, plaque morphology, implanted devices, etc.). That said, only about 20% of interventional cardiologists in the United States use IVI imaging in conjunction with coronary angiography during PCI procedures. Additionally, IVI imaging uses the mating of disposable single use sterile catheters or probes to non-disposable imaging systems. The mating process involves mechanically connecting the catheter/probe to a system to get an adequate electrical, optical, and/or radio frequency (RF) connection (e.g., in addition to or alternatively to a mechanical connection) depending on the type of catheter/probe. However, the mating step/process is not always robust and may fail in one or more situations. Failure of this mating step may lead to procedure delay and user frustration among other issues.

Where a signal is very small, it may be hard to measure. Additionally, where a signal is not location specific (e.g., a signal may be from all reflections making it back to a system), it may be unclear if the signal is from a fully mated probe/catheter, a partially mated probe/catheter, or reflection(s) from an endface of a probe connector of the probe/catheter.

While a sensor may be used to determine if the probe/catheter is mechanically mated with a system, drawbacks are that the use of the sensor uses an additional means or component(s) to interface with the sensor for each probe/catheter, and such a method is an indirect method of determining the mechanical connection and only determines if there is a mechanical connection.

Interferometry methods such as OFDR (Optical Frequency Domain Reflectometer) and OTDR (Optical Time Domain Reflectometer) may be used in telecom networks to measure insertion loss and return loss from fiber optic interfaces including connectors. The drawback of this method is that it requires a specialized complex hardware to measure insertion loss and/or return loss signals from the interfaces. Additionally, these methods are not used to determine or guide a mating process since they are slow. Such methods also require a completely different instrument.

Other methods may potentially check reflections at a distal tip of an optical probe/catheter. However, such a technique does not guarantee knowledge of acceptable or complete/full mating since a strength of the reflections may not be necessarily known a priori. This method would only serve to guess connection status and would not be useable to guide the mating process.

Performing a pullback when a probe is not properly mated may yield useless or less useful data, and may cause a physician a lot of wasted time. Likewise, if the automatic disconnection of the probe/catheter fails, the user, unaware, may attempt to remove the probe/catheter from the system just to be left, for example, with the core connected to a patient interface unit (PIU) of the system, potentially rendering the system unusable and/or causing damage to the PIU.

Accordingly, detecting, monitoring, and guiding the mating step (e.g., engagement, disengagement, etc.) would be desirable to increase likelihood of catheter/probe mating success (e.g., to reduce mating failure(s), to minimize mating failure(s), to avoid mating failure(s), etc.), to confirm mating status, and to reduce case delays and user frustration. It also would be desirable to provide one or more probe/catheter detecting, monitoring, and/or guiding techniques and/or structure for use in at least one optical device, assembly or system to achieve consistent, reliable detection, monitor, and guidance results at high efficiency and a reasonable cost of manufacture and maintenance.

SUMMARY OF THE DISCLOSURE

Accordingly, it is a broad object of the present disclosure to provide imaging (e.g., OCT, NIRAF, etc.) apparatuses, systems, methods and storage mediums for using and/or controlling one or more imaging modalities and/or to detect, monitor, and/or guide a mating step or process of a probe/catheter with one or more imaging apparatuses, systems, storage mediums, etc. It is also a broad object of the present disclosure to provide OCT devices, systems, methods and storage mediums using an interference optical system, such as an interferometer (e.g., spectral-domain OCT (SD-OCT), swept-source OCT (SS-OCT), multimodal OCT (MM-OCT), Intravascular Ultrasound (IVUS), Near-Infrared Autofluorescence (NIRAF), Near-Infrared Spectroscopy (NIRS), Near-Infrared Fluorescence (NIRF), therapy modality using light, sound, or other source of radiation, etc.).

Other broad objects of the present disclosure are to minimize, reduce, and/or avoid engagement and disengagement failures and to have a robust means of determining status of probe/catheter engagement to an apparatus or system (e.g., an imaging apparatus, an imaging system, etc.). Knowledge of probe engagement status may be used to communicate status to a user and to allow specific apparatus and/or system functionality and/or to inhibit other apparatus and/or system functionality.

One or more embodiments may obtain a direct analysis of a probe/catheter connection and/or mating process using at least one reliable optical interference signal. One or more embodiments may operate with or without prior knowledge of reflection strength(s) from probe/catheter distal reflections, and preferably do not require such knowledge of the reflection strength(s).

One or more embodiments of the present disclosure may use an OCT signal at a PIU output connector to determine engagement/disengagement status, and/or may use an OCT signal about or for the PIU output connector and a catheter connector to guide an engagement/disengagement process (also referred to herein as an "engagement process" or a "mating step or process").

One or more features of the present disclosure may be employed or exercised using any OCT apparatus and/or system, and may be done so using only minor modifications to the reference arm where an apparatus and/or system uses a single reference arm path, one or more embodiments of a method or technique of the present disclosure may use two reference arm paths or the ability to sufficiently adjust reference arm delay so as to adjust the imaging FOV to be at either the main sample imaging location or at about the system distal-most point (mating location).

One or more embodiments of a system for increasing imaging depth range may include: an OCT system; a reference reflection adjusted so that a reflection from a system mating connector is visible in an imaging field of view; and one or more processors that operate to determine if a catheter/probe is mated to the system mating connector.

In one or more embodiments, determining engagement status may include one or more of the following: (i) at a start of an engage process, an apparatus or system may switch from a main reference arm to an auxiliary reference arm; (ii) the apparatus or system may move a linear stage and a rotary motor to pre-engage positions; (iii) the apparatus or system may measure or use previously stored PIU output connector signal-to-noise ratio (SNR) pre-engagement; (iv) the apparatus or system may move the linear stage to an engage position; (v) the apparatus or system may measure PIU output connector SNR post-engagement; (vi) the apparatus or system may determine that the engagement is successful or acceptable if a Post-Engage SNR is different from the Pre-Engage SNR, and/or (vii) the apparatus or system confirms only one peak is present at or about the PIU output connector. One or more embodiments may measure a peak instead. Crosstalk noise may be used as a metric. One or more embodiments may use data from measured peak and noise levels of a single or several A-lines. In one or more embodiments, once an engagement process starts, mechanical mating of a sacrificial interface to a catheter connector may be attempted.

In one or more embodiments, determining disengagement status may include one or more of the following: (i) at a start of a disengage process, an apparatus or system may switch from a main reference arm to an auxiliary reference arm; (ii) the apparatus or system may move a linear stage and a rotary motor to pre-disengage positions; (iii) the apparatus or system may measure or use previously stored PIU output connector signal-to-noise ratio pre-disengage (SNR); (iv) the apparatus or system may move the linear stage to a disengage position; (v) the apparatus or system may measure PIU output connector SNR post-disengagement; (vi) the apparatus or system may determine that the disengagement is successful or acceptable if a Post-Disengage SNR is different from the Pre-Disengage SNR, and/or (vii) the apparatus or system confirms a second peak is present at a distance from the PIU output connector about equal to the distance between pre-disengage and engage positions. One or more embodiments may measure a peak instead. Crosstalk noise may be used as a metric. One or more embodiments may use data from measured peak and noise levels of a single or several A-lines. In one or more embodiments, once a disengagement process starts, mechanical disengaging of a sacrificial interface from a catheter connector may be attempted.

In one or more embodiments, guiding engagement may include one or more of the following: (i) at a start of an engage process, an apparatus or system may switch from a main reference arm to an auxiliary reference arm; (ii) the apparatus or system may move a linear stage and a rotary motor to pre-engage positions; (iii) the apparatus or system may slowly move the linear stage to an engage position while measuring distance between a PIU connector reflection and a catheter connector reflection; (iv) the apparatus or system may use distance between the two reflections (e.g., the PIU connector reflection and the catheter connector reflection) to guide and determine when the Engage position is reached; (v) the apparatus or system may pull back (e.g., slowly, at a predetermined speed, etc.) the linear stage to release mechanical connection tension and to determine connection status; and/or (vi) the apparatus or system may determine that the engagement is successful or acceptable (or is likely successful/acceptable) in a case where only one peak is present (e.g., at or about the PIU output connector); otherwise, the engagement is deemed unsuccessful, and the apparatus or system may repeat the steps from step (iii).

In one or more embodiments, guiding disengagement may include one or more of the following: (i) at a start of a disengage process, an apparatus or system may switch from a main reference arm to an auxiliary reference arm; (ii) the apparatus or system may move a linear stage and a rotary motor to pre-disengage positions; (iii) the apparatus or system may move (e.g. slowly, at a predetermined speed, etc.) the linear stage to a Disengage position; (iv) the apparatus or system may pull off (e.g., slowly, at a predetermined speed, etc.) the linear stage from the Disengage position; (v) the apparatus or system may confirm a second peak is present at a distance from a PIU output connector commensurate with the distance expected from pulling off the linear stage; and/or (vi) the apparatus or system may perform a second pull of the linear stage, and, in the event that two peaks are present and represent expected separation, then the disengage is likely successful or acceptable; otherwise, disengage is deemed unsuccessful, and the apparatus or system may repeat the steps from step (iii).

One or more embodiments of the present disclosure may include one or more of the following: (i) an imaging system with an optical probe (e.g., where the imaging system may be configurable or may operate to switch between more than one reference arm); (ii) an auxiliary reference arm may be used to image using an OCT PIU Output Connector reflection; (iii) the auxiliary reference arm may be used to look at the PIU Output Connector to diagnose if/whether an Output Connector interface may benefit from replacement or maintenance (e.g., the interface may be dirty, damaged, etc.); and/or (iv) the auxiliary reference arm may be used to look at a PIU sacrificial connector to diagnose and/or aid catheter/probe engagement and/or disengagement. One or more embodiments may include one or more of the following: (i) determining whether the sacrificial interface needs to be cleaned, maintained, or replaced (e.g., the interface may be dirty, damaged, etc.); (ii) using crosstalk noise as a metric for engagement and/or disengagement status; (iii) operating to work with lens-based connections in addition to or alternatively to connector-based connections; and/or (iv) using one or more features of different auxiliary arm embodiments discussed herein. In one or more embodiments, using an imaging system with an optical probe (e.g., where the imaging system may be configurable or may operate to switch between more than one reference arm) may improve or provide an advantage of detection of a fiber probe connection. In one or more embodiments, using interference light may permit detection of depth-resolved peaks. In one or more embodiments, guiding connection and/or disconnection of a probe/catheter may improve or optimize the process and may increase or maximize a respective success rate(s) (e.g., for connection, for disconnection, for both, etc.). One or more embodiments may include or may also include checking for probe connector quality as the connector approaches. In one or more embodiments, the auxiliary reference arm may be used to do one or more of the following: (i) look at a rotation or Rotary Junction (RJ) connector interface as well as sacrificial interface and RJ Optical interfaces; and/or (ii) determine optical health of the PIU and determine system optical performance in a predictable manner.

One or more embodiments of the present disclosure detect, monitor, and/or guide a mating step (e.g., engagement, disengagement, etc.) or process of a probe/catheter. In one or more embodiments, catheter/probe mating success is increased or maximized, mating success may be confirmed, and/or case delays and user frustration are reduced or minimized.

In one or more embodiments, intraluminal imaging may be used to acquire high-resolution cross-sectional images of tissues or materials, and to enable real time visualization. Intraluminal imaging may employ automatic connection and disconnection of an optical probe/catheter to an imaging system. In one or more embodiments, knowing a status of the probe/catheter connection improves or maximizes system performance/functionality. One or more embodiments properly mate and/or confirm proper mating of the probe/catheter connection to yield useful data, and to improve or maximize time of a physician.

One or more embodiments of the present disclosure of at least one procedure may be described using at least one or more flow diagram. The present disclosure describes one or more features of one or more embodiments of methods in detail, including, but not limited to, about how to detect a lumen edge pixel in an A-line, how to detect an initial lumen edge pixel candidate corresponding peak(s) in an A-line (e.g., using neighborhood connectivity to join peaks into one or more objects), how to identify the edge pixels caused by image artifacts in an OCT image, and how to form the final lumen edge of the imaged vessel.

Accordingly, it is at least one broad object of the present disclosure to provide one or more optical apparatuses, systems, methods (for using and/or manufacturing) and storage mediums, such as, but not limited to, fiber optic catheters, endoscopes and/or optical coherence tomography (OCT) apparatuses and systems, and methods and storage mediums, for use with same, to achieve consistent, reliable detection and/or guidance results (e.g., determining engagement status, determining disengagement status, guiding engagement, guiding disengagement, etc.), including at a high efficiency, and at a reasonable cost of manufacture and maintenance.

One or more additional objects of the present disclosure are to one or more of: (i) avoid using global threshold(s) in a two-dimensional (2D) image in one or more embodiments; and/or (ii) combine pixel intensity values and the separated gradient along A-line values and gradient across the A-lines values together for edge detection to improve lumen edge detection accuracy in one or more embodiments and/or to improve detection of a reflection from one or more of the catheter, PIU, or an interface created by the catheter and PIU when connected or made to come together in one or more embodiments. For example, in one or more embodiments of avoiding the use of global threshold(s), 2D image processing may be decoupled into separated 1D signal processing, and an adaptive threshold may be used for each one dimensional (1D) signal (i.e., A-line) of the image in polar coordinate(s) for lumen edge detection.

In one or more embodiments, a one-dimensional A-line signal may reveal more information about the underlying signal. Lumen edge pixel and artifact pixels may be easily identified using the A-line signal. Preferably, in one or more embodiments, each one-dimensional data (A-line) has its own optimal threshold for lumen edge detection. Such feature(s) remove(s) the need of finding global optimal threshold(s) in a 2D image, and reduces the computation complexity. One or more of the subject features also reduce(s) the algorithm sensitivity to regional image intensity variation, and/or provides immunity to intensity variation due to the imaging angle and distance changes.

In one or more embodiments, an optical coherence tomography system for determining engagement and/or disengagement status and/or for guiding engagement and/or disengagement may include: a light source that operates to produce a light; an interference optical system that operates to: (i) receive and divide the light from the light source into a first light with which an object or sample is to be irradiated and a second reference light, (ii) send the second reference light for reflection off of a reference mirror of the interference optical system, and (iii) generate interference light by causing reflected or scattered light of the first light with which the object or sample has been irradiated and the reflected second reference light to combine or recombine, and/or to interfere, with each other, the interference light generating one or more interference patterns; and one or more detectors that operate to continuously acquire the interference light and/or the one or more interference patterns.

In one or more embodiments, a computer-readable storage medium may store at least one program that operates to cause one or more processors to execute a method for determining engagement and/or disengagement status and/or for guiding engagement and/or disengagement, where the method may include one or more steps discussed herein.

In accordance with one or more embodiments of the present disclosure, apparatuses and systems, and methods and storage mediums for determining engagement and/or disengagement status and/or for guiding engagement and/or disengagement may further operate to characterize biological objects, such as, but not limited to, blood, mucus, tissue, etc.

It should be noted that one or more embodiments of the method(s) for determining engagement and/or disengagement status and/or for guiding engagement and/or disengagement, and/or other methods, of the present disclosure may be used in other imaging systems, apparatuses or devices, where images are formed from signal reflection and scattering within tissue sample(s) using a scanning probe. For example, IVI modalities, such as IVUS, may be used where IVI or IVUS images may be processed in addition to or instead of OCT images.

One or more embodiments of the present disclosure may be used in clinical application(s), such as, but not limited to, intervascular imaging, atherosclerotic plaque assessment, cardiac stent evaluation, balloon sinuplasty, sinus stenting, arthroscopy, ophthalmology, ear research, veterinary use and research, etc.

In accordance with at least another aspect of the present disclosure, one or more technique(s) discussed herein may be employed to reduce the cost of at least one of manufacture and maintenance of the one or more apparatuses, devices, systems and storage mediums by reducing or minimizing a number of optical components and by virtue of the efficient techniques to cut down cost of use/manufacture of such apparatuses, devices, systems and storage mediums.

According to other aspects of the present disclosure, one or more additional devices, one or more systems, one or more methods and one or more storage mediums using, or for use with, one or more engagement and/or disengagement status determination and/or engagement and/or disengagement guidance techniques are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIGS. 3A-3J are diagrams of respective apparatus/system embodiments for performing engagement and/or disengagement status determination and/or engagement and/or disengagement guidance techniques in accordance with one or more aspects of the present disclosure;

DETAILED DESCRIPTION OF THE PRESENT DISCLOSURE

One or more devices/apparatuses, optical systems, methods, and storage mediums for performing engagement and/or disengagement status determination and/or engagement and/or disengagement guidance techniques are disclosed herein.

Figure 1:
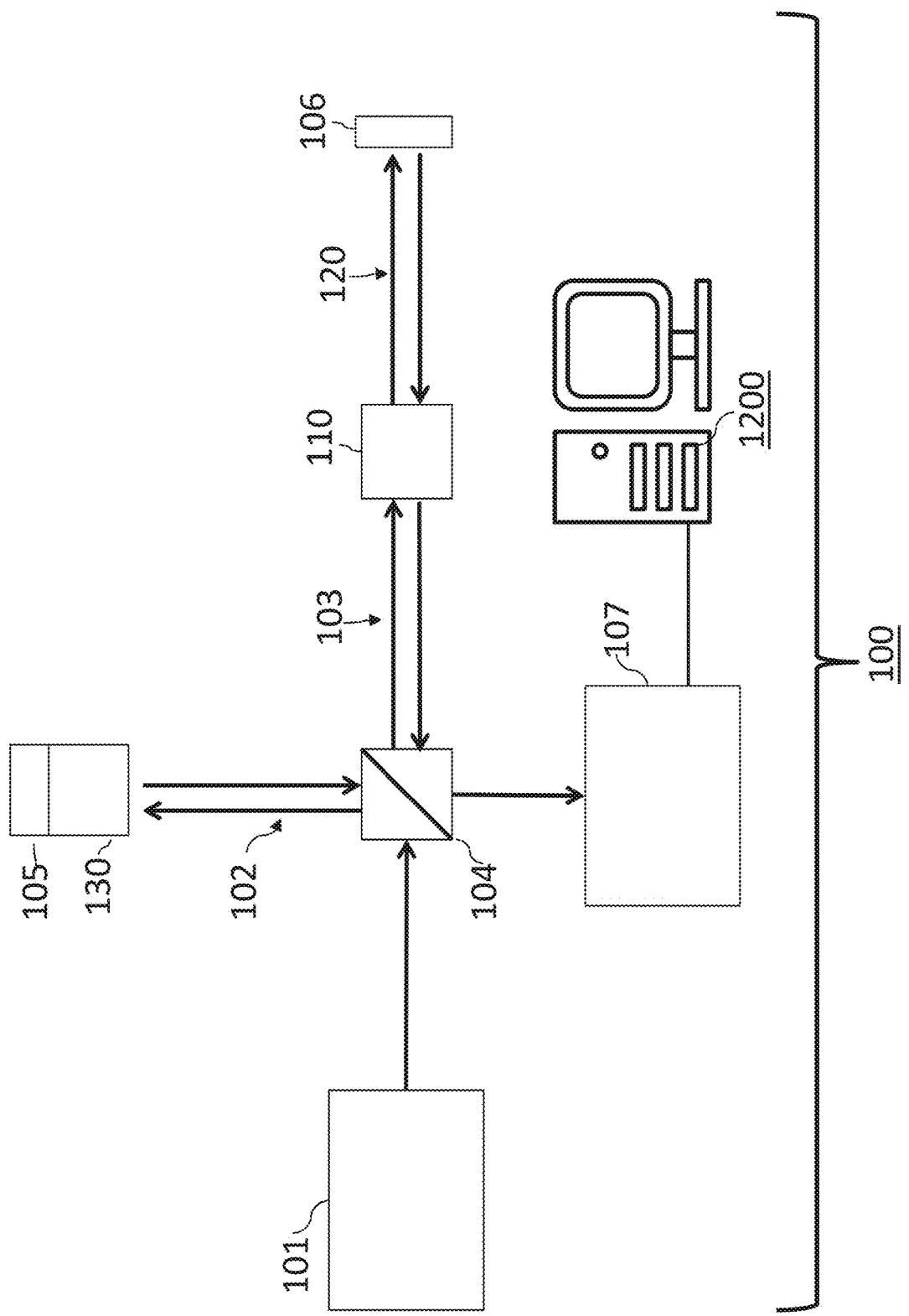
FIG. 1 is a diagram showing an embodiment of a system which can utilize one or more engagement and/or disengagement status determination and/or engagement and/or disengagement guidance techniques in accordance with one or more aspects of the present disclosure.

Turning now to the details of the figures, FIG. 1 shows an OCT system 100 (as referred to herein as "system 100" or "the system 100") which operates to utilize an OCT technique, including, but not limited to, one or more embodiments of engagement and/or disengagement status determination and/or engagement and/or disengagement guidance techniques discussed herein, with optical probe applications in accordance with one or more aspects of the present disclosure. The system 100 comprises a light source 101, a reference arm 102, a sample arm 103, a splitter 104 (also referred to herein as a "beam splitter"), a reference mirror (also referred to herein as a "reference reflection") 105, and one or more detectors 107. The system 100 may include a phase shift device or unit 130, and, in one or more embodiments, the phase shift device or unit may be omitted. In one or more embodiments, the system 100 may include a patient interface device or unit ("PIU") 110 and a catheter 120 (as diagrammatically shown in FIGS. 1-2), and the system 100 may interact with a sample or target 106 (e.g., via the catheter/probe 120 and/or the PIU 110). In one or more embodiments, the system 100 includes an interferometer, or an interferometer is defined by one or more components of the system 100, such as, but not limited to, at least the light source 101, the reference arm 102, the sample arm 103, the splitter 104, and the reference mirror 105.

The light source 101 operates to produce a light to the splitter 104, which splits the light from the light source 101 into a reference beam passing into the reference arm 102 and a sample beam passing into the sample arm 103. The beam splitter 104 is positioned or disposed at an angle to the reference mirror 105, the one or more detectors 107 and to the sample or target 106. The reference beam goes through the phase shift unit 130 (when included in a system, as shown in the system 100), and the reference beam is reflected from the reference mirror 105 in the reference arm 102 while the sample beam is reflected or scattered from a sample 106 through the PIU (patient interface unit; also referred to herein as a patient interface component (PIC)) 110 and the catheter 120 in the sample arm 103. Both of the reference and sample beams combine (or recombine) at the splitter 104 and generate interference patterns. The output of the system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 1200, 1200' (shown in FIG. 15 or FIG. 16, respectively, discussed further below). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

The light source 101 may include a plurality of light sources or may be a single light source. The light source 101 generates broadband laser lights in one or more embodiments. The light source 101 may include one or more of a laser, an organic Light-Emitting Diode (OLED), a Light-Emitting Diode (LED), a halogen lamp, an incandescent lamp, supercontinuum light source pumped by a laser, and/or a fluorescent lamp. The light source 101 may be any light source that provides light which can then be split up into at least three bands in which each band is further dispersed to provide light which is then used to for spectral encoding of spatial information. The light source 101 may be fiber coupled or may be free space coupled to the other components of the system or systems discussed herein, such as, but not limited to, the system 100, the system 100', the system 100", the system 100''', etc.

In accordance with at least one aspect of the present disclosure, a feature of OCT systems is implemented using fiber optics. As aforementioned, one application of an OCT technique of the present disclosure is to use OCT with a catheter 120 as schematically shown in FIGS. 1-2.

Figure 2:
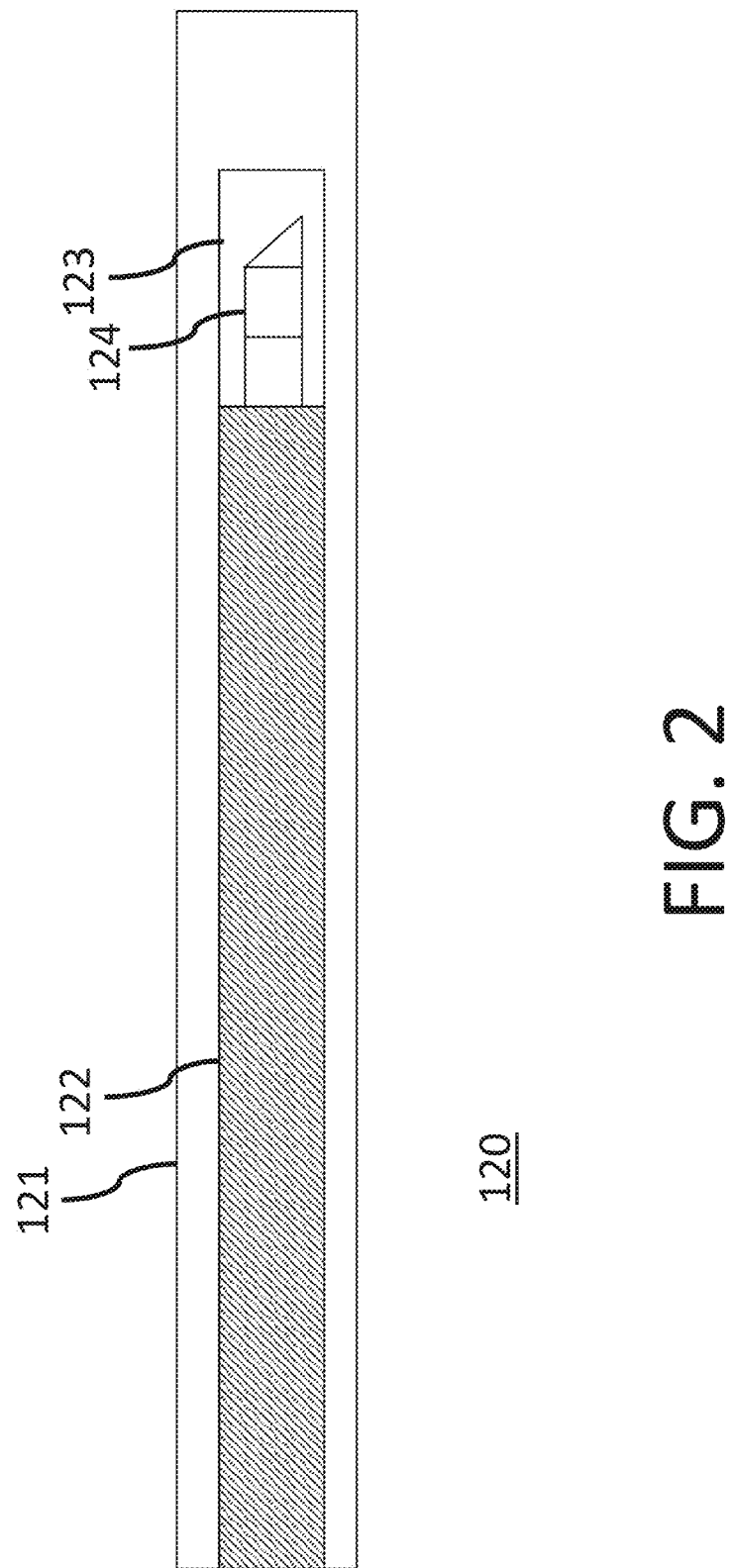
FIG. 2 is a diagram of an embodiment of a catheter that may be used with at least one embodiment of an apparatus or system for performing engagement and/or disengagement status determination and/or engagement and/or disengagement guidance techniques in accordance with one or more aspects of the present disclosure.

FIG. 2 shows an embodiment of the catheter 120 including a sheath 121, a coil 122, a protector 123 and an optical probe 124. As shown schematically in FIGS. 1-2, the catheter 120 preferably is connected to the PIU 110 to spin the coil 122 with pullback (e.g., at least one embodiment of the PIU 110 operates to spin the coil 122 with pullback). The coil 122 delivers torque from a proximal end to a distal end thereof (e.g., via or by a rotational motor in the PIU 110). In one or more embodiments, the coil 122 is fixed with/to the optical probe 124 so that a distal tip of the optical probe 124 also spins to see an omnidirectional view of a biological organ, sample or material being evaluated, such as, but not limited to, hollow organs such as vessels, a heart, etc. For example, fiber optic catheters and endoscopes may reside in the sample arm (such as the sample arm 103 as shown in FIG. 1) of an OCT interferometer in order to provide access to internal organs, such as intravascular images, gastrointestinal tract or any other narrow area, that are difficult to access. As the beam of light through the optical probe 124 inside of the catheter 120 or endoscope is rotated across the surface of interest, cross-sectional images of one or more samples are obtained. In order to acquire three-dimensional data, the optical probe 124 is simultaneously translated longitudinally during the rotational spin resulting in a helical scanning pattern. This translation may be performed by pulling the tip of the probe 124 back towards the proximal end and therefore referred to as a pullback.

In one or more embodiments, the patient user interface 110 may comprise or include a connection component (or interface module), such as a rotary junction, to connect one or more components, such as one or more components of a probe (e.g., a catheter 120 (see e.g., FIGS. 1-2)), a needle, a capsule, a patient interface unit or component (e.g., the patient interface unit or component 110), etc., to one or more other components, such as, an optical component, a light source (e.g., the light source 101), a deflection section (e.g., such as the deflection or deflected section, which is a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc.), the sample arm 102, a motor that operates to power the connection component and/or the patient user interface 110, etc. For example, when the connection member or interface module is a rotary junction, preferably the rotary junction operates as discussed below). In one or more other embodiments, the rotary junction may be at least one of: a contact rotary junction, a lenseless rotary junction, a lens-based rotary junction, or other rotary junction known to those skilled in the art.

In at least one embodiment, the PIU 110 may include a Fiber Optic Rotary Junction (FORJ), a rotational motor and translation motorized stage (e.g., a portion of the PIU 110), and a catheter connector (e.g., a portion of the PIU 110). The FORJ allows uninterrupted transmission of an optical signal while rotating a fiber along the fiber axis. The FORJ may have a free space optical beam combiner including a rotor and stator.

Descriptions of like-numbered elements present in the system 100' and already described above, such as for the system 100, shall not be repeated, and are incorporated by reference herein in their entireties.

In at least one embodiment, the console 1200, 1200' operates to control motions of a motor and translation motorized stage (hereinafter referred to as "motor" or "motor and stage"), acquires intensity data from the at least one detector(s) 107, and displays the scanned image (e.g., on a monitor or screen such as a display, screen or monitor 1209 as shown in the console 1200 of FIG. 15 and/or the console 1200' of FIG. 16 as further discussed below). In one or more embodiments, the console 1200, 1200' operates to change a speed of the motor and/or to stop the motor. The motor may be a stepping or a DC servo motor to control the speed and increase position accuracy.

In one or more embodiments, the console or computer 1200, 1200' operates to control the system 100 (and other systems, such as, but not limited to, the system 100', the system 100", the system 100''', etc. as discussed further below), the catheter 120 and/or one or more other above-described components of the system 100. In at least one embodiment, the console or computer 1200, 1200' operates to acquire intensity data from the at least one detector 107 of the OCT system/device/apparatus, and displays the image(s) (e.g., on a monitor or screen such as a display, screen or monitor 1209 as shown in the console 1200 of FIG. 15 and/or the console 1200' of FIG. 16 as further discussed below). The output of the one or more components of the system 100 (and other systems, such as, but not limited to, the system 100', the system 100", the system 100''', etc. as discussed further below) is acquired with the at least one detector 107 of the OCT system/device/apparatus, e.g., such as, but not limited to, photodiodes, Photomultiplier tube(s) (PMTs), line scan camera(s), or multi-array camera(s). Electrical analog signals obtained from the output of the system 100 (and/or other systems, such as, but not limited to, the system 100', the system 100", the system 100''', etc. as discussed further below) or one or more components thereof are converted to digital signals to be analyzed with a computer, such as, but not limited to, the computer 1200, 1200' (e.g., as shown in FIGS. 1, 3A-3J, 11-13, and 15-16). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector 107 comprises three detectors configured to detect three different bands of light.

In one or more embodiments, one or more imaging techniques may be used, such as, but not limited to, various OCT imaging techniques, lumen edge detection, stent strut detection, and/or artifact detection techniques, and other techniques as discussed in at least U.S. Pat. App. No. 62/901,472, which is incorporated by reference herein in its entirety, and as discussed in U.S. patent application Ser. No. 16/990,800, filed on Aug. 11, 2020, which is incorporated by reference herein in its entirety. In one or more embodiments of the present disclosure, an OCT image is formed in a polar coordinate system from A-lines. Each A-line includes much information about the imaged object, such as, but not limited to: clear indications of artifacts from metal objects (e.g., stents, stent struts, guide wires, PIU reflection, catheter/probe reflection, noise artifacts, etc.) like narrow signal width and/or sharp rising and falling edges; significant difference in signal intensity and shape for unobstructed soft tissue compared to the sheath reflection and other artifacts like wide signal width and a gentle falling edge. Each A-line may represent a cross-sectional 1D sampling of a target, sample, object, etc., such as, but not limited to, a vessel, along a certain view angle. As an imaging probe or device rotates (e.g., rotates about 0 to about 360 degrees, about 180 degrees to about 360 degrees, about 360 degrees, etc.), the corresponding A-lines form the complete two-dimensional (2D) cross-section of the target, sample, object, etc. (e.g., the vessel) in polar coordinates, which is then converted into Cartesian coordinates to form the tomographical-view (tomo-view) image of the cross-section of the target, sample, object, etc. (e.g., the vessel).

In accordance with at least one aspect of the present disclosure and as aforementioned, one or more additional methods for lumen, stent, and/or artifacts detection of OCT images are provided herein and are discussed in U.S. patent application Ser. No. 16/414,222, filed on May 16, 2019, the entire disclosure of which is incorporated by reference herein in its entirety, and in U.S. Pat. Pub. No. 2019/

0374109, which was published on Dec. 12, 2019, the disclosure of which is incorporated by reference herein in its entirety.

Regardless of the approach, a predetermined or determined threshold may be used to detect the most significant pulse that may be corresponding to the lumen edge (in one or more embodiments, the most significant pulse denotes the maximum peak and its associated front edge also named as "major peak/edge"; such data may contain or include artifact edge pixels) in a specific A-line in one or more embodiments. Any pulse above the threshold is an edge pulse of an object candidate. The largest pulse among all the candidates in terms of area under the pulse is considered to be the maximum peak (also referred to herein as the "most significant pulse", or the "major peak/edge", etc.).

One or more embodiments of the present disclosure may minimize, reduce, and/or avoid engagement and disengagement failures and may have a robust means of determining status of probe/catheter engagement to an apparatus or system (e.g., an imaging apparatus, an imaging system, etc.). Knowledge of probe engagement status may be used to communicate status to a user and to allow specific apparatus and/or system functionality and/or to inhibit other apparatus and/or system functionality.

One or more embodiments may obtain a direct analysis and indication of a probe/catheter connection and/or mating process using at least one reliable optical interference signal. One or more embodiments may operate with or without prior knowledge of reflection strength(s) from probe/catheter distal reflections, and preferably do not require such knowledge of the reflection strength(s).

One or more embodiments of the present disclosure may use an OCT signal at a PIU output connector to determine engagement/disengagement status, and/or may use an OCT signal about or for the PIU output connector and a catheter connector to guide an engagement/disengagement process (also referred to herein as an "engagement process" or a "mating step or process"). One or more processors discussed herein may operate in one or more modes (e.g., an engagement mode, a disengagement mode, an engagement and disengagement mode, combinations thereof, etc.). For example, one or more processors may operate in multiple modes (or one of a plurality modes), where, in one or more embodiments, a first mode is an engagement mode and a second mode is a disengagement mode.

One or more features of the present disclosure may be employed or exercised using any OCT apparatus and/or system, and may be done so using only minor modifications to the reference arm where an apparatus and/or system uses a single reference arm path, one or more embodiments of a method or technique of the present disclosure may use two reference arm paths or the ability to sufficiently adjust reference arm delay so as to adjust the imaging FOV to be at either the main sample imaging location or at about the system distal-most point (mating location).

One or more embodiments of a system for increasing imaging depth range may include: an OCT system; a reference reflection adjusted so that a reflection from a system mating connector is visible in an imaging field of view; and one or more processors that operate to determine if a catheter/probe is mated to the system mating connector.

Now turning to the details of FIGS. 3A-3J, diagrams of respective apparatus/system embodiments are shown for performing engagement and/or disengagement status determination and/or engagement and/or disengagement guidance techniques in accordance with one or more aspects of the present disclosure.

FIGS. 3A-3J depict several different embodiments of OCT interferometer apparatuses/systems with retro-reflection paths for main OCT imaging and for auxiliary OCT imaging in accordance with one or more aspects of the present disclosure. As shown via the reference numbers in FIGS. 3A-3J, while not limited to such examples, one or more of the subject apparatuses or systems may have the same or similar components (or one or more of the same or similar components) as other apparatuses or systems discussed herein. For example, one or more apparatuses may have a light source 101, a splitter 104 or deflecting section 108, one or more circulators 901, a reference arm 102, a sample arm 103, a PIU 110, a catheter or probe 120, a reference reflector 105, a detector (e.g., a photo-receiver, a photo diode, etc.) 107, a computer, processor or other type of data acquisition unit (DAQ) (e.g., computer or processor 1200, computer or processor 1200', etc.), etc. Numerous non-limiting, non-exhaustive embodiment examples of such components are discussed throughout the disclosure with reference to at least FIGS. 1, 11-13, and 15-16, and detail(s) of one or more embodiments of one or more of such components will not be repeated with reference to FIGS. 3A-3J. The discussions of FIGS. 3A-3J, as shown below, will focus primarily (but not solely) on structural modification(s), difference(s), or other variation(s) that may be used for one or more detection and guidance of optical connection(s) techniques discussed herein.

Figure 3A:
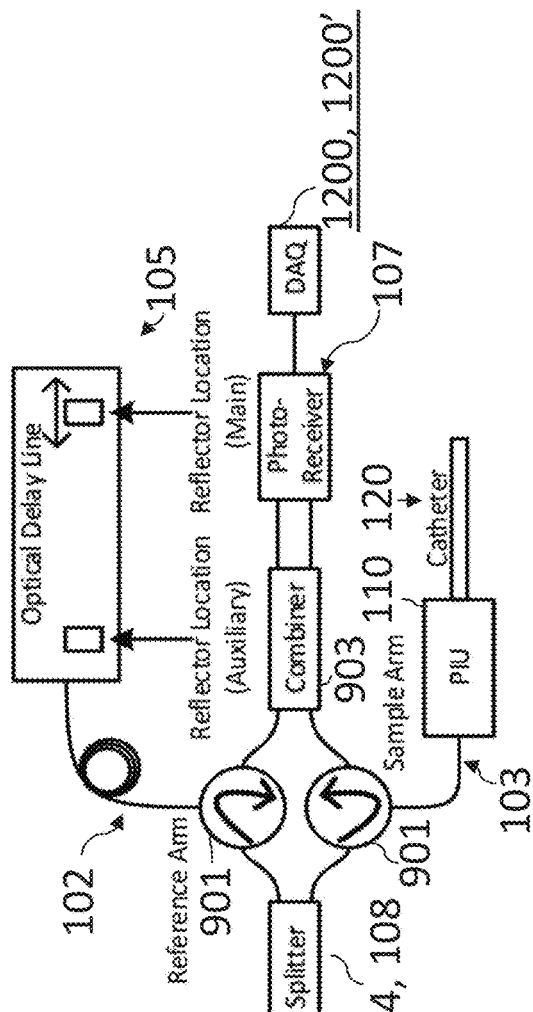

FIG. 3A depicts a reference arm 102 that makes use of an optical delay line (e.g., a long optical delay line). The optical delay line has sufficient adjustment to cover at least the length of the probe or catheter 120. When the delay is increased in one or more embodiments, the reference path or arm 102 may match the length of the sample path or arm 103 with the probe or catheter 120 included and may permit regular OCT system imaging. In one or more embodiments, when the delay is decreased, the reference path or arm 102 may match the length of the sample path or arm 103 without the probe or catheter 120 and may permit OCT imaging of the system to a catheter connection region.

Figure 3B:
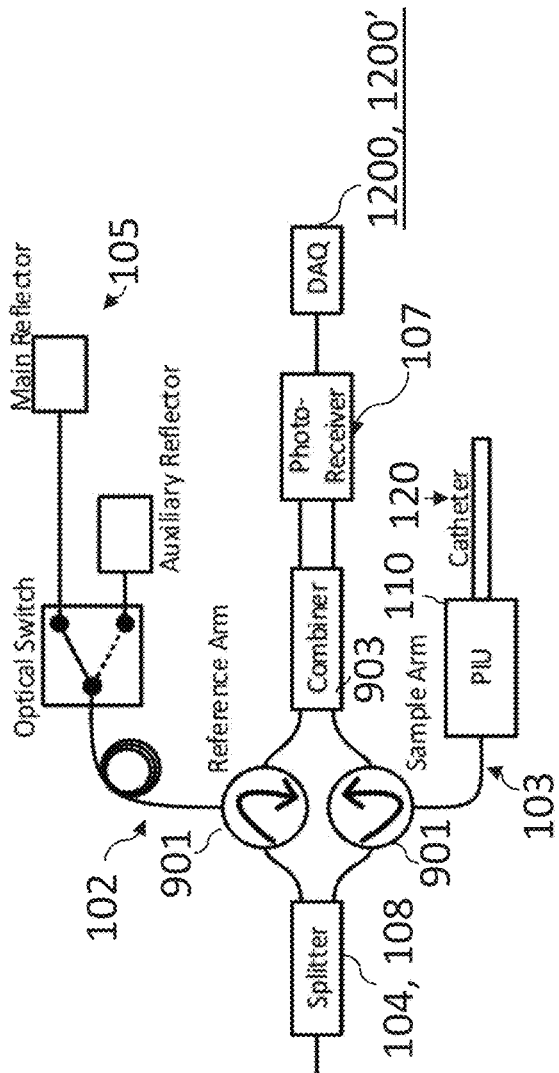

FIG. 3B depicts an optical power-efficient reference arm 102 that makes use of a 1×2 optical switch. The optical switch main output port is part of the main reference path or arm 102 and the secondary port constitutes, or is, part of the auxiliary reference path or arm (see split in the reference arm 102 of FIG. 3B). In one or more embodiments, the main reference path or arm 102 may match the length of the sample path or arm 103 with the probe or catheter 120 included and may permit regular OCT system imaging. In one or more embodiments, the auxiliary reference path may match the length of the sample path or arm 103 without the probe or catheter 120 and may permit OCT imaging of the system to the catheter connection region.

Figure 3C:
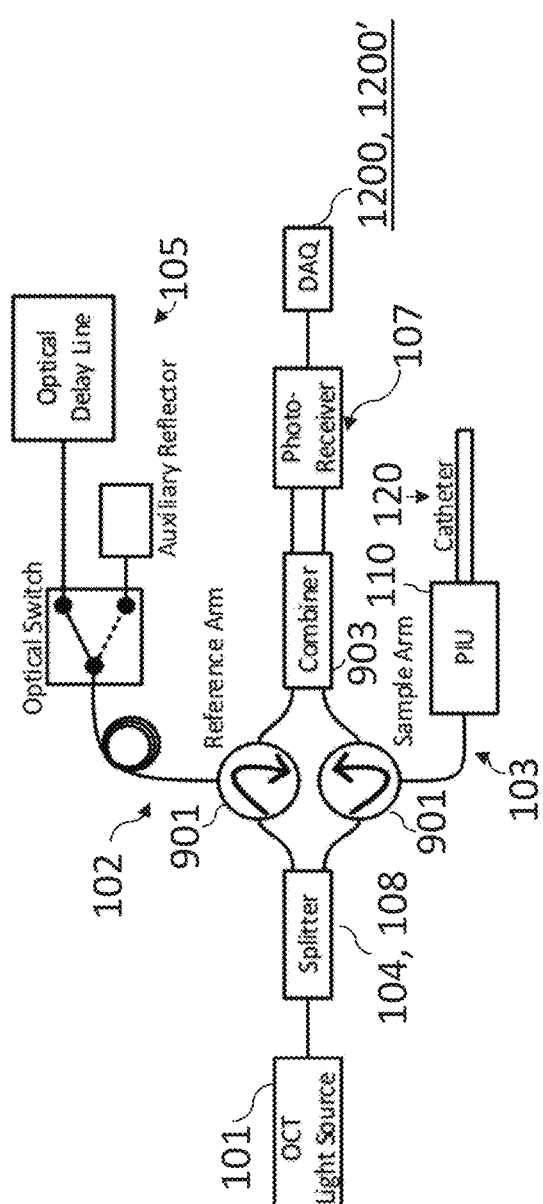

FIG. 3C depicts a similar apparatus/system to the one from FIG. 3B, where the main reflector is replaced with an optical delay line. The optical delay line allows adjustment of the main reference arm 102 to account for catheters/probes (e.g., the catheter or probe 120) with varying optical lengths.

Figure 3D:
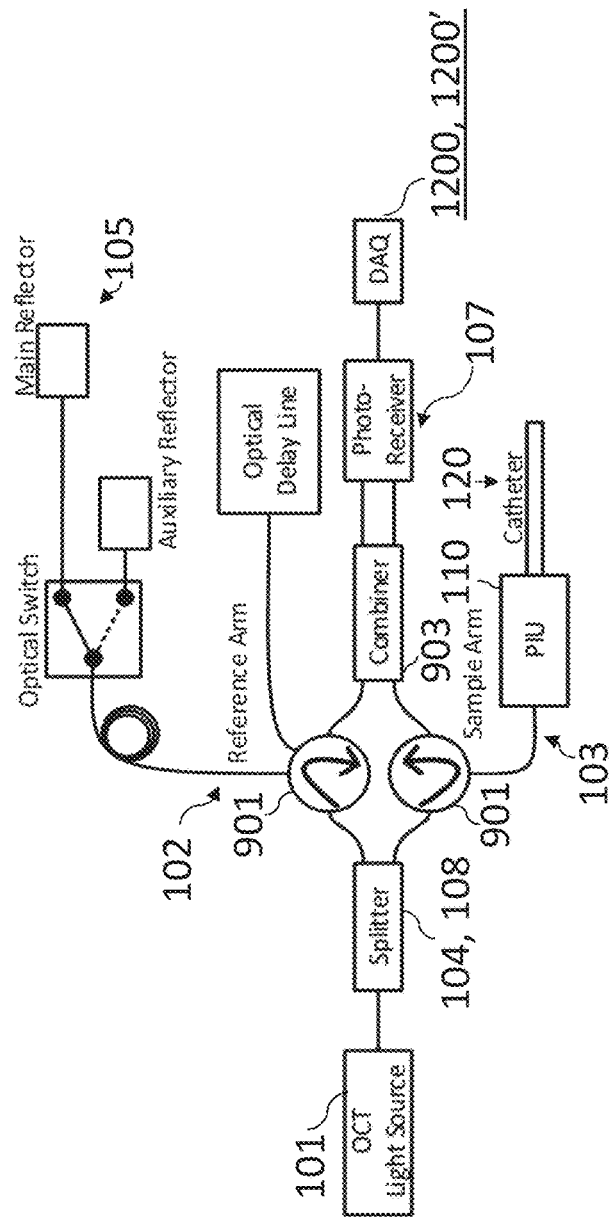

FIG. 3D depicts a similar system to the one from FIG. 3B, where the reference arm makes use of a 4-port circulator (see e.g., the top circulator 901 in the embodiment of FIG. 3D) instead of a 3-port circulator. The extra port allows for the use of an optical delay line. The optical delay line allows in this case for adjustment of both the main and the auxiliary reference arms to account for catheters/probes (e.g., the catheter or probe 120 in FIG. 3D) with varying optical lengths and to address manufacturing tolerances of the system/apparatus interferometer including replacement of PIUs (e.g., PIU 110 of FIG. 3D) with different lengths.

Figure 3E:
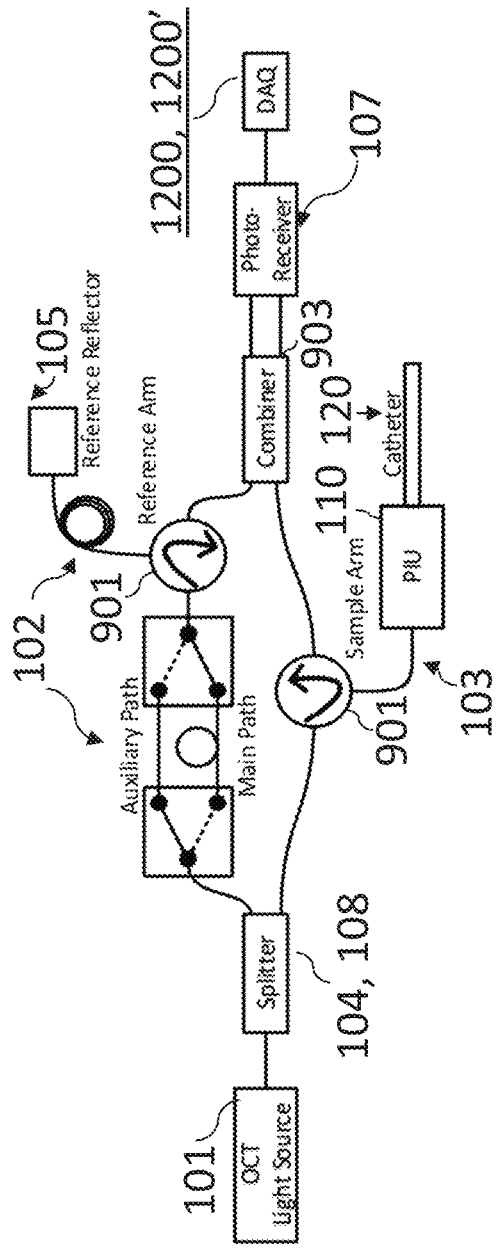

FIG. 3E depicts a similar apparatus/system to the one from FIG. 3B, where the main and auxiliary reference arms of the reference arm 102 are delineated by the use of two 1×2 optical switches in series. The reference reflector (e.g., the reference reflector 105) in this case may be a fixed reflector or an optical delay line.

Figure 3F:
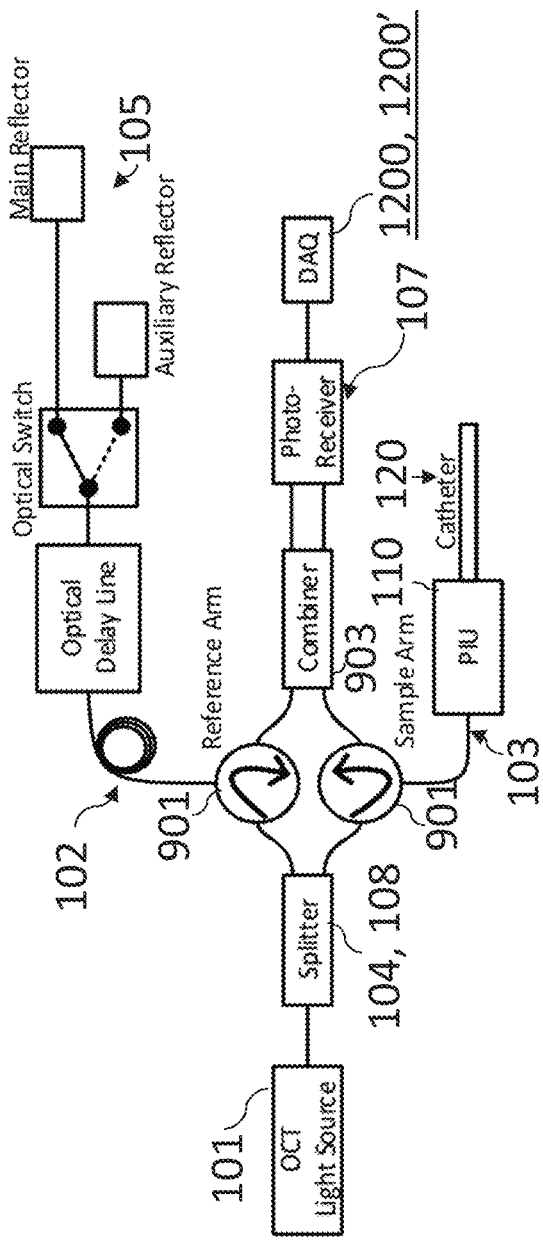

FIG. 3F depicts a similar apparatus/system to the one from FIG. 3B, where the optical delay line is inserted in the reference arm 102 before the optical switch. The optical delay line allows, in this embodiment, for adjustment of both the main and the auxiliary reference arms of the reference arm 102 to account for catheters/probes (e.g., the catheter or probe 120) with varying optical lengths and to address manufacturing tolerances of the apparatus/system interferometer including replacement of PIUs (e.g., the PIU 110) with different lengths.

FIG. 3G depicts a similar apparatus/system to the one from FIG. 3B, where the optical delay line is used to adjust the optical length to match either the main reflector or the auxiliary reflector of the reference reflection 105. In at least one embodiment, light may be reflected from both reflectors of the reference reflection 105 at the same time so light efficiency may be reduced.

FIG. 3H depicts a similar apparatus/system to the one from FIG. 3B, where the apparatus/system of FIG. 3H additionally or alternatively may have two overlapping reflections. The apparatus or system may employ a rotary junction RJ and an optical coupler or combiner (e.g., the combiner 903) as shown.

Figure 3I:
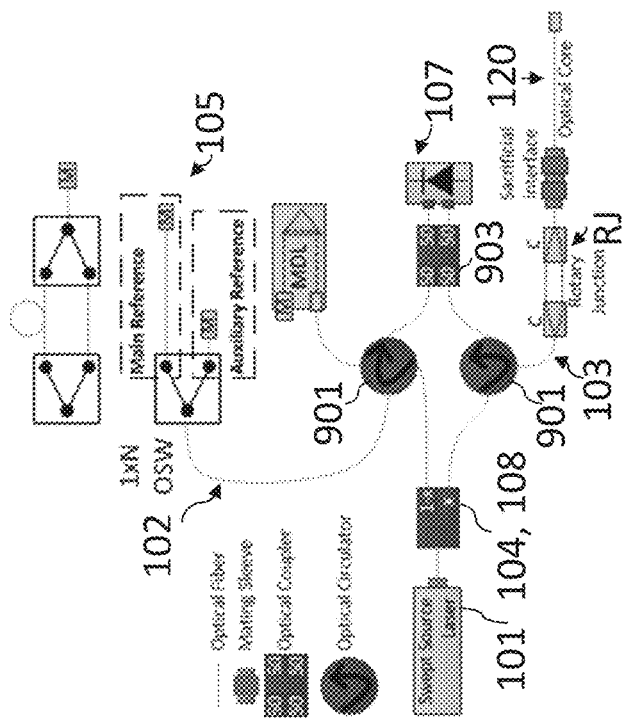

FIG. 3I depicts a similar apparatus/system to the one from FIG. 3D, where the apparatus/system of FIG. 3I also may use a four-port circulator (e.g., the top circulator 901 of FIG. 3I). The apparatus or system may employ a rotary junction RJ and an optical coupler or combiner (e.g., the combiner 903) as shown.

Figure 3J:
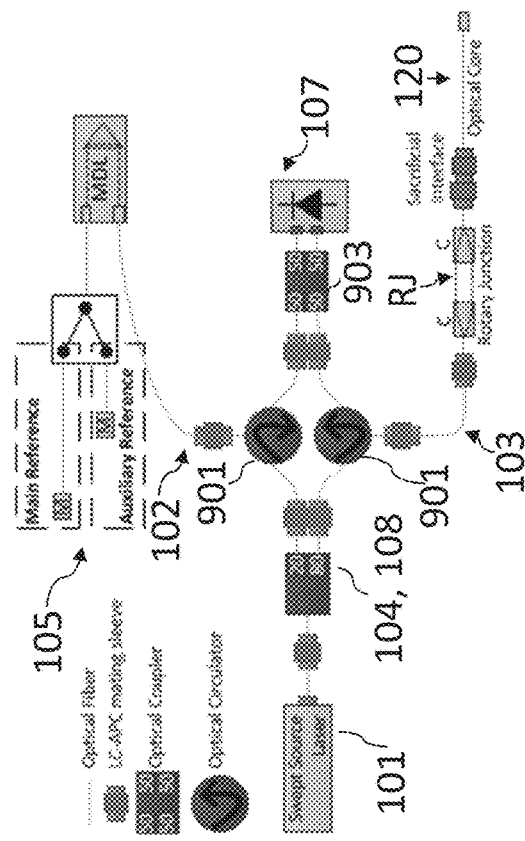

FIG. 3J depicts a similar apparatus/system to the one from FIG. 3F, where the apparatus/system of FIG. 3J is another embodiment that employs a transmission type delay line.

Figure 4:
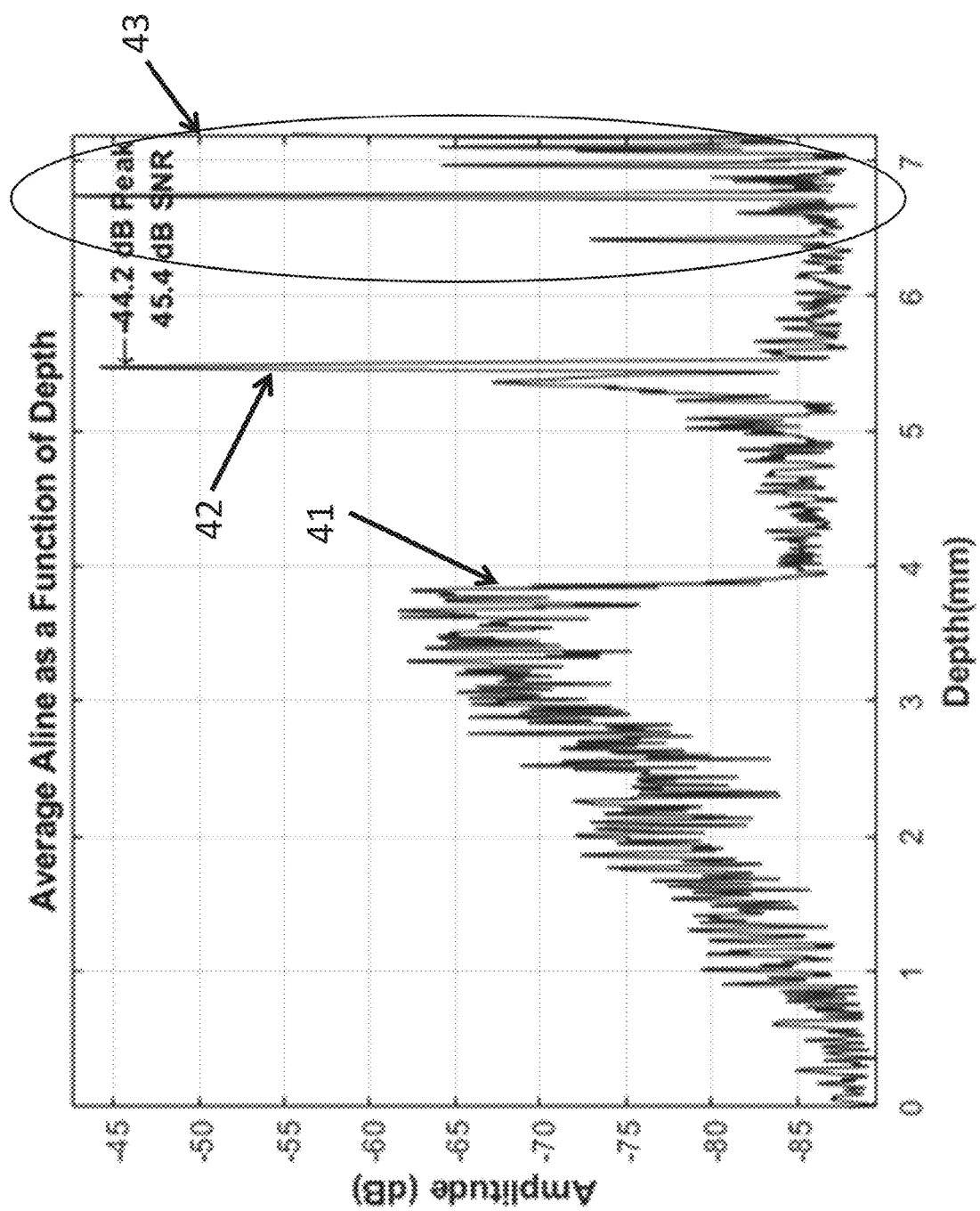
FIG. 4 is a graph showing average A-line as a function of depth in accordance with one or more aspects of the present disclosure.
Figure 5:
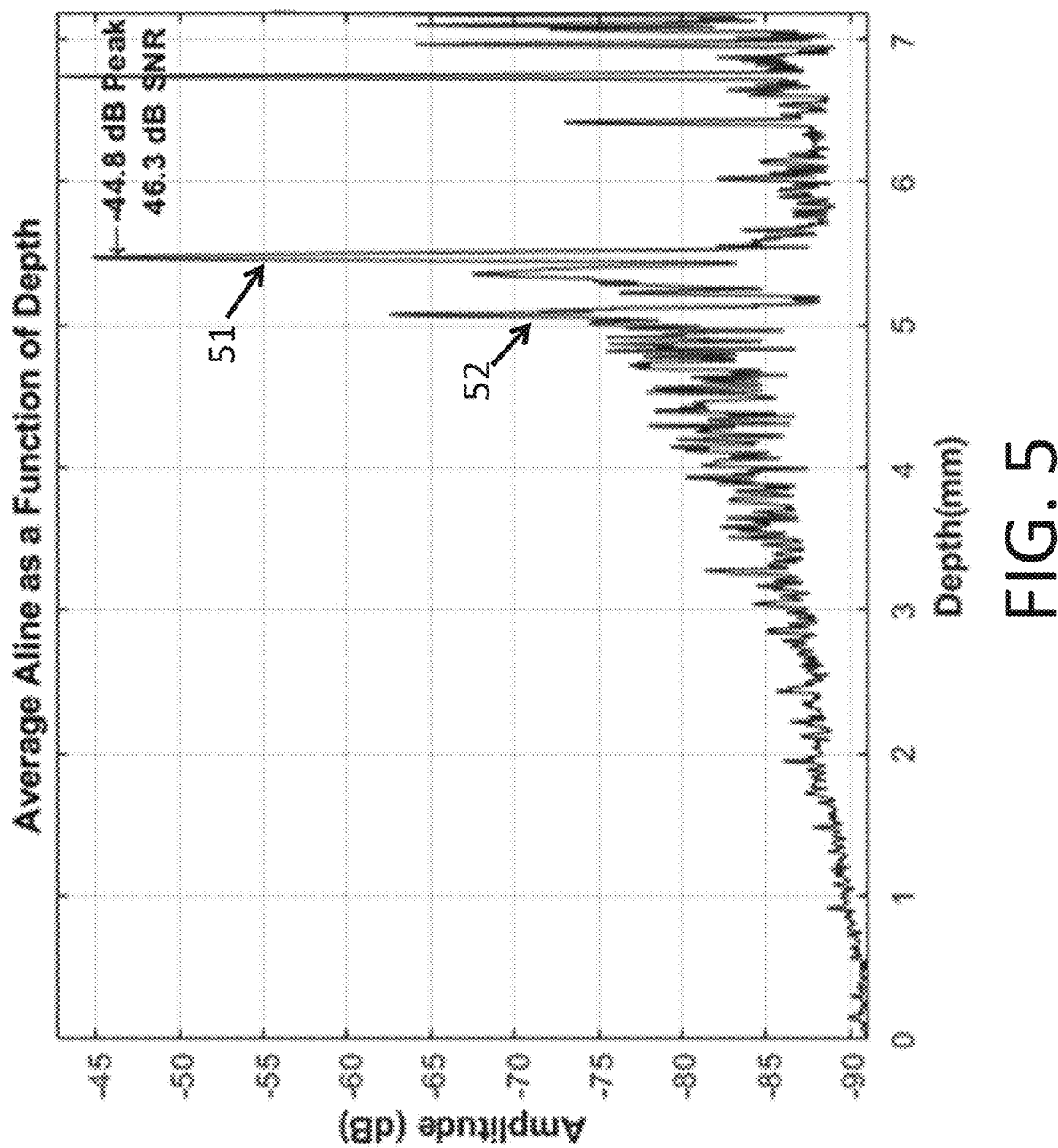
FIG. 5 is a graph showing average A-line as a function of depth in accordance with one or more aspects of the present disclosure.
Figure 6:
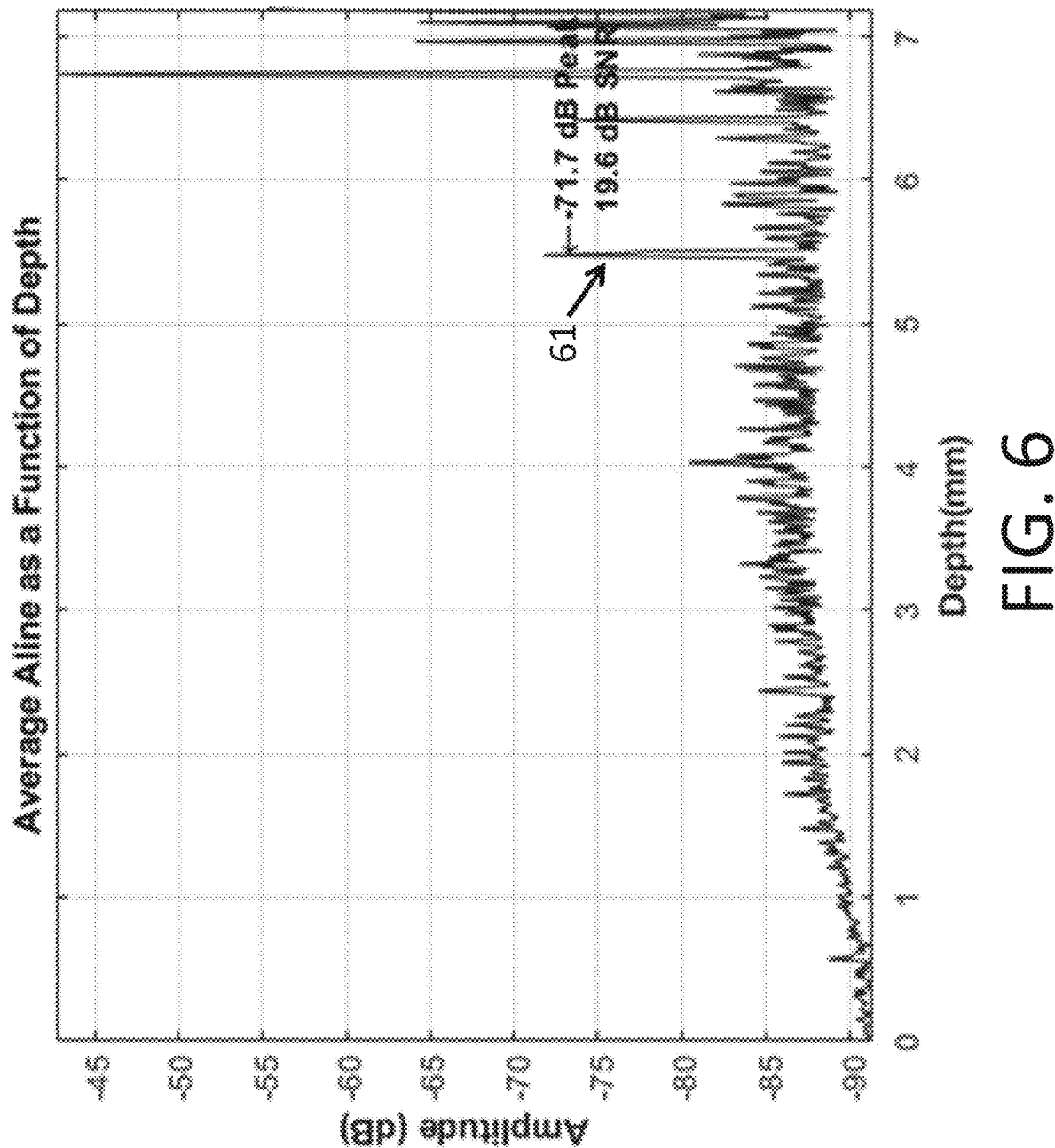
FIG. 6 is a graph showing average A-line as a function of depth in accordance with one or more aspects of the present disclosure.

FIG. 4 shows average A-line as a function of depth depicting the reflection from the PIU Output Connector and reflections from the catheter connector separated by 1.6 mm as the mating has not happened yet. One or more embodiments of an apparatus or system may use this information to guide the linear stage closer to the mating point. Point 41 shows a location on the A-line of a catheter reflection (see FIG. 4). As shown in FIG. 4, point 42 shows a location on the A-line of a PIU reflection, and noise artifacts are shown in area 43 of the A-line. FIG. 5 shows average A-line as a function of depth depicting the reflection from the PIU Output Connector and reflections from the Catheter Connector separated by 0.4 mm as the mating is getting closer to occurring. As shown in FIG. 5, point 51 shows a location on the A-line of a PIU reflection, and point 52 shows a location on the A-line of a catheter reflection. In one or more embodiments, the main reflection from the end face of the Catheter Connector may be better demarcated since the separation between the two connectors is small. FIG. 6 shows average A-line as a function of depth depicting the reflection from the mated PIU Output Connector and Catheter Connector merged into one since the mating has occurred (point 61 shows a location on the A-line of a reflection of the mated catheter/PIU connectors). By way of at least one example, in one or more embodiments of an engage (or engagement) process, the A-line signal may switch from the A-line shown in FIG. 4 to the A-line shown in FIG. 6 when the engagement is successful between the PIU and catheter (e.g., at the PIU output connector). In one or more embodiments of a disengagement process, the A-line signal may switch from the A-line in FIG. 6 to the A-line in FIG. 4. In one or more embodiments of an engagement process, the A-line signal may switch from the A-line of FIG. 4 to the A-line of FIG. 5, and then from the A-line of FIG. 5 to the A-line of FIG. 6. In one or more embodiments of a disengagement process, the A-line signal may switch from the A-line in FIG. 6 to the A-line of FIG. 5, and then from the A-line of FIG. 5 to the A-line of FIG. 4.

Figure 7:
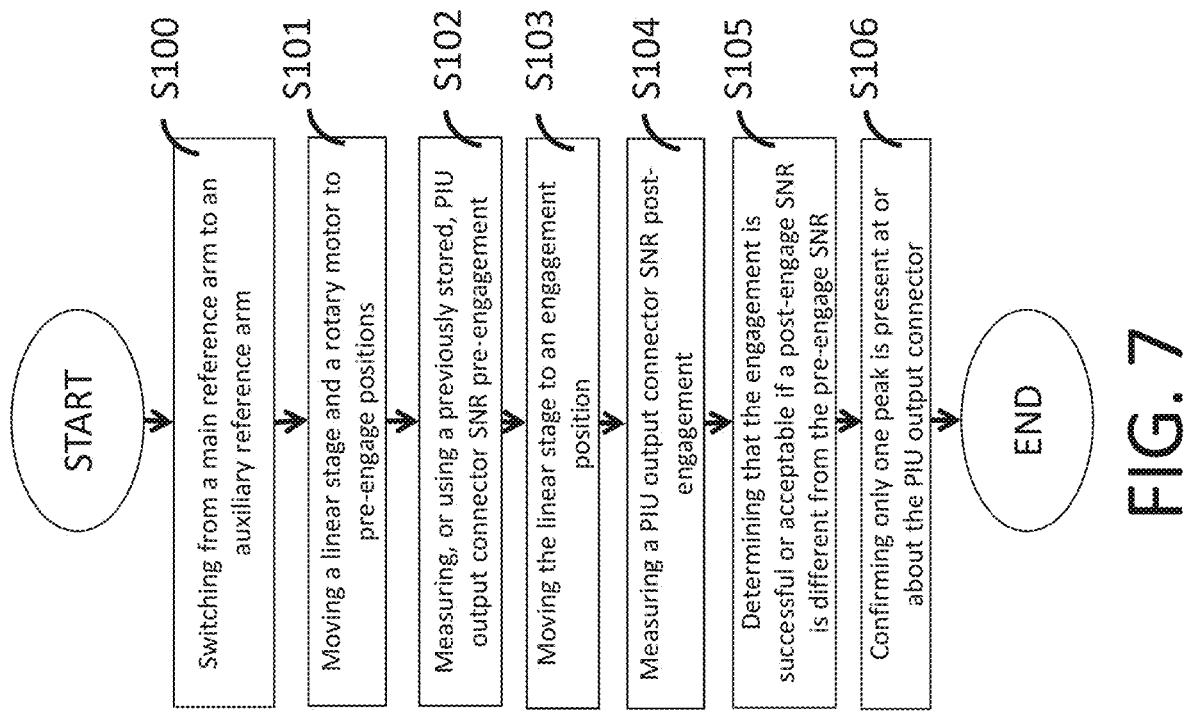
FIG. 7 is a flow diagram illustrating at least one method embodiment of performing an engagement guiding and/or status determination feature, function or technique in accordance with one or more aspects of the present disclosure.

At least one engagement determination method embodiment of the present disclosure describes steps (e.g., as shown in FIG. 7) that may be used to determine engagement status where, at a start of the process/method, an apparatus/system switches from the main reference arm path to the auxiliary reference arm path. In one or more embodiments, determining engagement status may include one or more of the following: (i) at a start of an engage process, an apparatus or system may switch from a main reference arm to an auxiliary reference arm (see e.g., step S100 in FIG. 7); (ii) the apparatus or system may move a linear stage and a rotary motor to pre-engage positions (see e.g., step S101 in FIG. 7); (iii) the apparatus or system may measure or use previously stored PIU output connector signal-to-noise ratio (SNR) pre-engagement ("pre-engage SNR") (see e.g., step S102 in FIG. 7); (iv) the apparatus or system may move the linear stage to an engage position (see e.g., step S103 in FIG. 7); (v) the apparatus or system may measure PIU output connector SNR post-engagement ("post-engage SNR") (see e.g., step S104 in FIG. 7); (vi) the apparatus or system may determine that the engagement is successful or acceptable if a post-engage SNR is different from the pre-engage SNR (see e.g., step S105 in FIG. 7), and/or (vii) the apparatus or system confirms only one peak is present at or about the PIU output connector (see e.g., step S106 in FIG. 7). One or more embodiments may measure a peak instead. Crosstalk noise may be used as a metric. One or more embodiments may use data from measured peak and noise levels of a single or several A-lines. In one or more embodiments, once an engagement process starts, mechanical mating of a sacrificial interface to a catheter connector may be attempted. In one or more embodiments, the apparatus/system may move the linear stage and rotary motor to pre-engage positions and may measure or use a previously stored, unmated PIU output connector signal to noise ratio or pre-engage SNR. The apparatus/system then may move the linear stage to an engage position, and may measure the PIU Output Connector post-engage SNR. Engagement may be deemed successful, in one or more embodiments, in a case where the post-engage SNR is different from the pre-engage SNR and/or in a case where the apparatus/system confirms that only one peak is present at or about where the PIU Output Connector peak is expected. FIG. 4 shows average A-line as a function of depth depicting the reflection from the PIU output connector and reflections from the catheter connector at about 5.4 mm imaging depth. FIG. 6 shows average A-line as a function of depth depicting the reflection from the mated PIU Output Connector and Catheter Connector at about 5.4 mm imaging depth. In this example, the reflection peak SNR has changed substantially from about 46 dB to about 20 dB (see e.g., FIG. 6).

Figure 8:
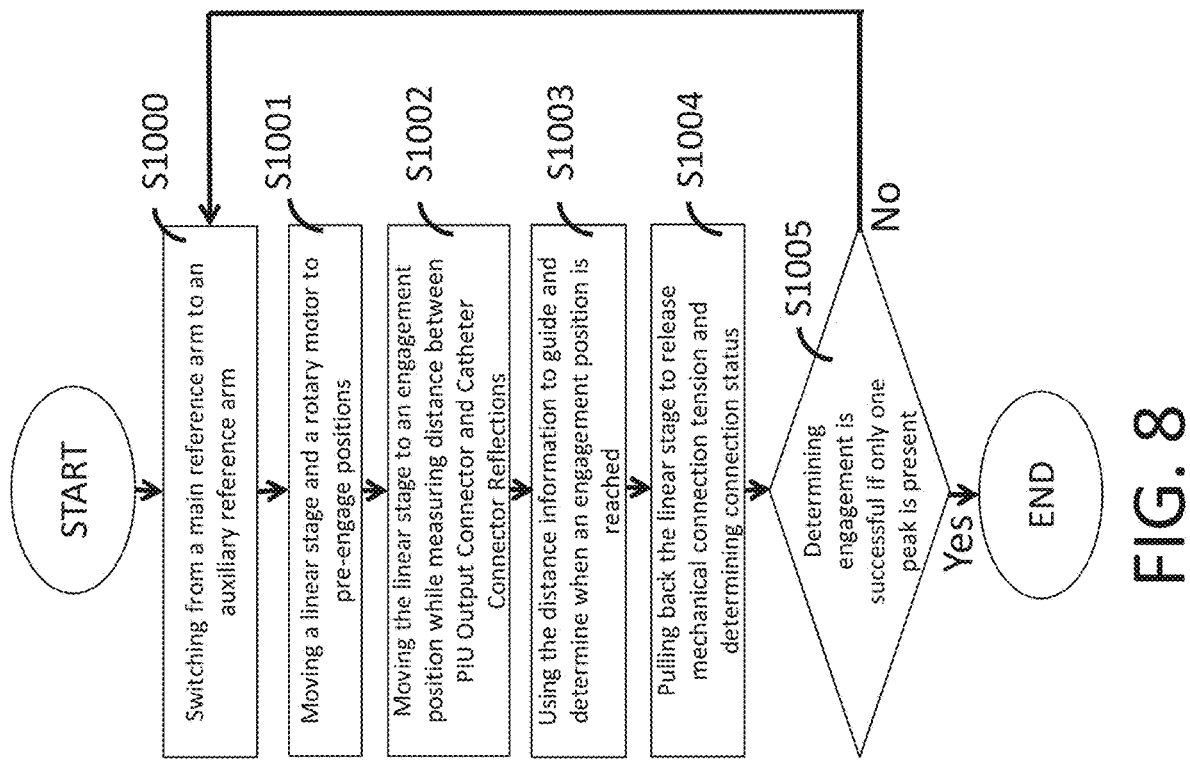
FIG. 8 is a flow diagram illustrating at least one method embodiment of performing an engagement guiding and/or status determination feature, function or technique in accordance with one or more aspects of the present disclosure.

At least one engagement determination method embodiment of the present disclosure describes steps (e.g., as shown in FIG. 8) that may be used to determine engagement status where, at a start of the process/method, an apparatus/system switches from the main reference arm path to the auxiliary reference arm path. The subject embodiment may use the same or similar devices/apparatuses, systems, and/or other hardware as that of any of the aforementioned embodiments. In one or more embodiments, determining engagement status may include one or more of the following: (i) at a start of an engage process, an apparatus or system may switch from a main reference arm to an auxiliary reference arm (see e.g., step S1000 in FIG. 8); (ii) an apparatus or system may move the linear stage and rotary motor to Pre-Engage positions (see e.g., step S1001 in FIG. 8); (iii) the apparatus or system may then move the linear stage to an Engage position while measuring distance between PIU Output Connector and Catheter Connector Reflections (see e.g., step S1002 in FIG. 8); (iv) the apparatus or system may use the distance information to guide and determine when the Engage position is reached (see e.g., step S1003 in FIG. 8); (v) the apparatus or system may pull back (e.g., slowly, at a predetermined speed, etc.) the linear stage to release mechanical connection tension and determine connection status (see e.g., step S1004 in FIG. 8); and/or (vi) the apparatus or system may determine that the engagement is successful or acceptable (or is likely successful/acceptable) in a case where only one peak is present (e.g., at or about the PIU output connector) (see e.g., step S1005 in FIG. 8); otherwise, the engagement is deemed unsuccessful, and the apparatus or system may repeat the steps from any of the aforementioned steps (e.g., from step (i), from step (ii), from step (iii), etc.).

Figure 9:
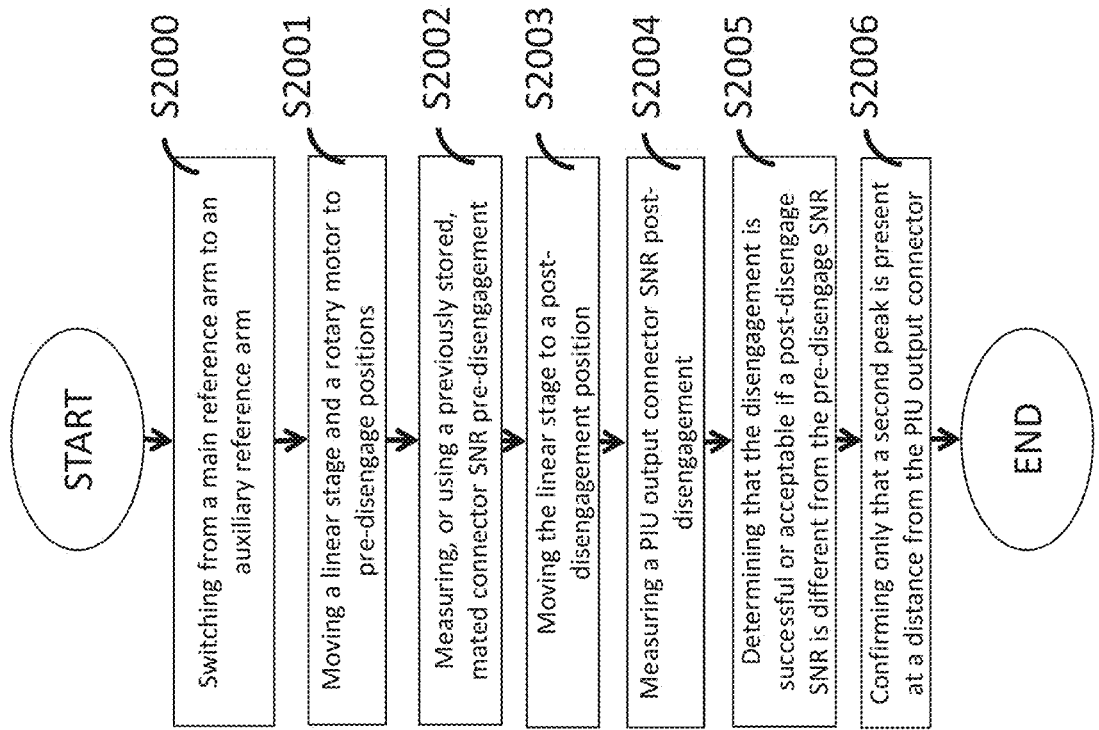
FIG. 9 is a flow diagram illustrating at least one method embodiment of performing a disengagement guiding and/or status determination feature, function or technique in accordance with one or more aspects of the present disclosure.

At least one disengagement determination method embodiment of the present disclosure describes steps (e.g., as shown in FIG. 9) that may be used to determine disengagement status where, at a start of the process/method, an apparatus/system switches from the main reference arm path to the auxiliary reference arm path. The subject embodiment may use the same or similar devices/apparatuses, systems, and/or other hardware as that of any of the aforementioned embodiments. In one or more embodiments, determining disengagement status may include one or more of the following: (i) an apparatus or system may switch from a main reference arm to an auxiliary reference arm (see e.g., step S2000 in FIG. 9); (ii) the apparatus or system may move the linear stage and rotary motor to Pre-Disengage positions (see e.g., step S2001 in FIG. 9), and (iii) may measure or use a previously stored mated connector signal to noise ratio "Pre-Disengage SNR" (see e.g., step S2002 in FIG. 9); and (iv) the apparatus or system may move the linear stage to a Post-Disengage position (see e.g., step S2003 in FIG. 9), and (v) may measure a PIU Output Connector Post-Disengage SNR "Post-Disengage SNR" (see e.g., step S2004 in FIG. 9). In one or more embodiments, disengagement may be deemed successful in a case where Post-Disengage SNR is different from Pre-Disengage SNR (see e.g., step S2005 in FIG. 9) and/or in a case where the apparatus or system confirms that a second peak is present at a distance from the PIU Output Connector about equal to the distance between Pre-Disengage and Post-Disengage positions or about where the Catheter Connector peak is expected (see e.g., step S2006 in FIG. 9). FIG. 4 shows average A-line as a function of depth depicting the reflection from the mated PIU Output Connector and catheter connector at about 5.4 mm imaging depth. FIG. 6 shows average A-line as a function of depth depicting the reflection from the mated PIU Output Connector and Catheter Connector at about 5.4 mm imaging depth. In at least this embodiment example, the reflection peak SNR may change substantially from about 20 dB to about 46 dB.

Figure 10:
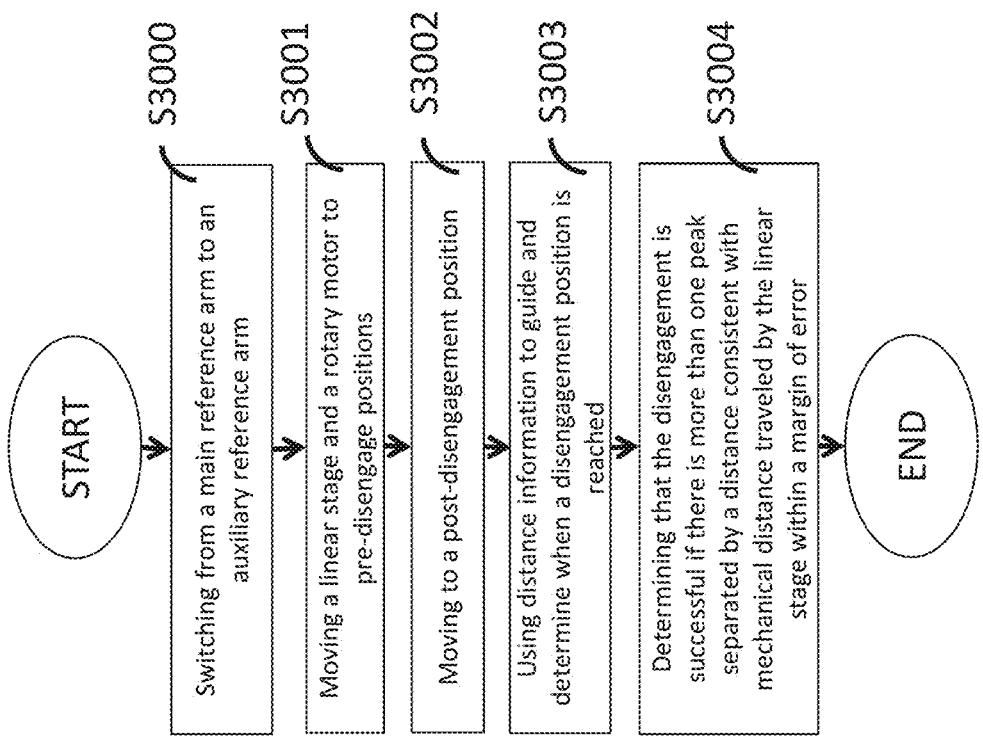
FIG. 10 is a flow diagram illustrating at least one method embodiment of performing a disengagement guiding and/or status determination feature, function or technique in accordance with one or more aspects of the present disclosure.

At least one disengagement determination method embodiment of the present disclosure describes steps (e.g., as shown in FIG. 10) that may be used to determine disengagement status where, at a start of the process/method, an apparatus/system switches from the main reference arm path to the auxiliary reference arm path (see e.g., step S3000 in FIG. 10). The subject embodiment may use the same or similar devices/apparatuses, systems, and/or other hardware as that of any of the aforementioned embodiments. In one or more embodiments, determining disengagement status may include one or more of the following: (i) the apparatus or system may move the linear stage and rotary motor to Pre-Disengage positions (see e.g., step S3001 in FIG. 10); (ii) the apparatus or system may then move to the Post-Disengage location (see e.g., step S3002 in FIG. 10), and may use distance information as the apparatus or system returns to a Post-Disengage position (see e.g., step S3003 in FIG. 10), ensuring that the prominent peaks are diverging consistent with the distance expected given the position of the PIU linear stage. In one or more embodiments, disengagement may be deemed successful in the event that there is more than one peak separated by a distance consistent with the mechanical distance traveled by the linear stage within a margin of error (see e.g., step S3004 in FIG. 1). FIG. 6 shows average A-line as a function of depth depicting the reflection from the mated PIU Output Connector and Catheter Connector merged into one as apparatus or system, or portion thereof, would be at the Pre-Disengage positions. Once the apparatus or system, or portion thereof, reaches the Disengage position, the apparatus or system (or portion thereof) moves away from the Disengage position, checking that the average A-line changes to resemble FIG. 5 as the two end faces begin to disengage shown at a distance of 0.4 mm separation. FIG. 4 shows average A-line as a function of depth depicting the reflection from the PIU Output Connector and reflections from the Catheter Connector separated by 1.6 mm once the PIU linear stage has reached its Post-Disengage position, 1.6 mm in this example, confirming that the probe has been successfully Disengaged.

Peak value may be used instead of SNR for all embodiments. Also, a single A-line, or two or more averaged A-lines, may be used to determine a peak (or peaks) and/or SNR in one or more embodiments.

The PIU linear stage actuation causes no change in optical length in one or more of the embodiment designs discussed herein, and this also may apply to apparatuses or systems where the total length of the signal path changes as the linear stage of the PIU moves. In one or more embodiments, an optical delay line may be used in an application similar to the embodiments and applications shown in FIGS. 3A, 3D, and 3F, and the optical delay line may move proportional to the linear stage of the PIU keeping the imaging depth consistently at the end face of the PIU-Catheter interface.

The Optical Delay line as depicted in FIGS. 3D and 3F may be used to maintain imaging depth as the PIU linear stage moves, changing the optical length from the module to the PIU-Catheter interface.

In one or more embodiments, determining disengagement status may include one or more of the following: (i) at a start of a disengage process, an apparatus or system may switch from a main reference arm to an auxiliary reference arm; (ii) the apparatus or system may move a linear stage and a rotary motor to pre-disengage positions; (iii) the apparatus or system may measure or use previously stored PIU output connector signal-to-noise ratio pre-disengage (SNR); (iv) the apparatus or system may move the linear stage to a disengage position; (v) the apparatus or system may measure PIU output connector SNR post-disengagement; (vi) the apparatus or system may determine that the disengagement is successful or acceptable if a Post-Disengage SNR is different from the Pre-Disengage SNR, and/or (vii) the apparatus or system confirms a second peak is present at a distance from the PIU output connector about equal to the distance between pre-disengage and engage positions. One or more embodiments may measure a peak instead. Crosstalk noise may be used as a metric. One or more embodiments may use data from measured peak and noise levels of a single or several A-lines. In one or more embodiments, once a disengagement process starts, mechanical disengaging of a sacrificial interface from a catheter connector may be attempted.

In one or more embodiments, guiding engagement may include one or more of the following: (i) at a start of an engage process, an apparatus or system may switch from a main reference arm to an auxiliary reference arm; (ii) the apparatus or system may move a linear stage and a rotary motor to pre-engage positions; (iii) the apparatus or system may slowly move the linear stage to an engage position while measuring distance between a PIU connector reflection and a catheter connector reflection; (iv) the apparatus or system may use distance between the two reflections (e.g., the PIU connector reflection and the catheter connector reflection) to guide and determine when the Engage position is reached; (v) the apparatus or system may pull back (e.g., slowly, at a predetermined speed, etc.) the linear stage to release mechanical connection tension and to determine connection status; and/or (vi) the apparatus or system may determine that the engagement is successful or acceptable (or is likely successful/acceptable) in a case where only one peak is present (e.g., at or about the PIU output connector); otherwise, the engagement is deemed unsuccessful, and the apparatus or system may repeat the steps from step (iii).

In one or more embodiments, guiding disengagement may include one or more of the following: (i) at a start of a disengage process, an apparatus or system may switch from a main reference arm to an auxiliary reference arm; (ii) the apparatus or system may move a linear stage and a rotary motor to pre-disengage positions; (iii) the apparatus or system may move (e.g. slowly, at a predetermined speed, etc.) the linear stage to a Disengage position; (iv) the apparatus or system may pull off (e.g., slowly, at a predetermined speed, etc.) the linear stage from the Disengage position; (v) the apparatus or system may confirm a second peak is present at a distance from a PIU output connector commensurate with the distance expected from pulling off the linear stage; and/or (vi) the apparatus or system may perform a second pull of the linear stage, and, in the event that two peaks are present and represent expected separation, then the disengage is likely successful or acceptable; otherwise, disengage is deemed unsuccessful, and the apparatus or system may repeat the steps from step (iii).

One or more embodiments of the present disclosure may include one or more of the following: (i) an imaging system with an optical probe (e.g., where the imaging system may be configurable or may operate to switch between more than one reference arm); (ii) an auxiliary reference arm may be used to image using an OCT PIU Output Connector reflection; (iii) the auxiliary reference arm may be used to look at the PIU Output Connector to diagnose if/whether an Output Connector interface may benefit from replacement or maintenance (e.g., the interface may be dirty, damaged, etc.); and/or (iv) the auxiliary reference arm may be used to look at a PIU sacrificial connector to diagnose and/or aid catheter/probe engagement and/or disengagement. One or more embodiments may include one or more of the following: (i) determining whether the sacrificial interface needs to be cleaned, maintained, or replaced (e.g., the interface may be dirty, damaged, etc.); (ii) using crosstalk noise as a metric for engagement and/or disengagement status; (iii) operating to work with lens-based connections in addition to or alternatively to connector-based connections; and/or (iv) using one or more features of different auxiliary arm embodiments discussed herein. In one or more embodiments, using an imaging system with an optical probe (e.g., where the imaging system may be configurable or may operate to switch between more than one reference arm) may improve or provide an advantage of detection of a fiber probe connection. In one or more embodiments, using interference light may permit detection of depth-resolved peaks. In one or more embodiments, guiding connection and/or disconnection of a probe/catheter may improve or optimize the process and may increase or maximize a respective success rate(s) (e.g., for connection, for disconnection, for both, etc.). One or more embodiments may include or may also include checking for probe connector quality as the connector approaches. In one or more embodiments, the auxiliary reference arm may be used to do one or more of the following: (i) look at a rotation or Rotary Junction (RJ) connector interface as well as sacrificial interface and RJ Optical interfaces; and/or (ii) determine optical health of the PIU and determine system optical performance in a predictable manner.

One or more embodiments of the present disclosure detect, monitor, and/or guide a mating step (e.g., engagement, disengagement, etc.) or process of a probe/catheter. In one or more embodiments, catheter/probe mating success is increased or maximized, mating success may be confirmed, and/or case delays and user frustration are reduced or minimized.

In one or more embodiments, intraluminal imaging may be used to acquire high-resolution cross-sectional images of tissues or materials, and to enable real time visualization. Intraluminal imaging may employ automatic connection and disconnection of an optical probe/catheter to an imaging system. In one or more embodiments, knowing a status of the probe/catheter connection improves or maximizes system performance/functionality. One or more embodiments properly mate and/or confirm proper mating of the probe/catheter connection to yield useful data, and to improve or maximize time of a physician.

One or more embodiments of the present disclosure of at least one procedure may be described using at least one or more flow diagram. The present disclosure describes one or more features of one or more embodiments of methods in detail, including, but not limited to, about how to detect a lumen edge pixel in an A-line, how to detect an initial lumen edge pixel candidate corresponding peak(s) in an A-line (e.g., using neighborhood connectivity to join peaks into one or more objects), how to identify the edge pixels caused by image artifacts in an OCT image, and how to form the final lumen edge of the imaged vessel.

Accordingly, it is at least one broad object of the present disclosure to provide one or more optical apparatuses, systems, methods (for using and/or manufacturing) and storage mediums, such as, but not limited to, fiber optic catheters, endoscopes and/or optical coherence tomography (OCT) apparatuses and systems, and methods and storage mediums, for use with same, to achieve consistent, reliable detection and/or guidance results (e.g., determining engagement status, determining disengagement status, guiding engagement, guiding disengagement, etc.), including at a high efficiency, and at a reasonable cost of manufacture and maintenance.

As aforementioned, FIGS. 4-6 show at least one embodiment of an Average A-line as a function of depth. In one or more embodiments, the A-line signal (e.g., as shown in each of FIGS. 4-6) may be processed in one or more ways, such as those ways, methods, techniques, etc. discussed in U.S. Pat. App. No. 62/944,064, filed on Dec. 5, 2019, the disclosure of which is incorporated by reference herein in its entirety, and discussed in U.S. patent application Ser. No. 17/098,042, filed on Nov. 13, 2020, the disclosure of which is incorporated by reference herein in its entirety. For example, one or more of the A-line signals may be smoothed by a 2D Gaussian filter for more reliable and accurate peak detection. Preferably, in one or more embodiments, special care or step(s) may be taken to avoid any phase delay introduced by any filtering so that the pulse location is not shifted. After such filtering, a much smoother A-line signal may be obtained. By way of at least another example, in one or more method embodiments, additional filtering (e.g., 1D filtering) may be performed to smooth A-lines. The pulse in the one-dimensional signal may correspond to a vessel wall. The rising edge of the pulse may be where the edge pixel of the A-line lies. By detecting the edge pixel in each A-line, the two-dimensional edge detection issue may be converted into a simpler one-dimensional pulse detection issue. In other words, one or more embodiments of the present disclosure may simplify at least one lumen edge, stent, and/or artifacts detection approach and provide a solution at the same time.

In one or more embodiments, an additional step of finding and calculating the peaks and width parameters for lumen edge, stent(s) and/or artifact(s) may be performed, for example, as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. In one or more embodiments, the peak or threshold (or other measurements/calculations) information may be applied to detecting and guiding one or more optical connections. In one or more embodiments, for each A-line signal, the highest peak may be detected within the proper FOV range. In at least one embodiment, there may be three (3) types of widths defined for the detected peak. The first may be a half-max width that may be detected using an adaptive threshold based on mean and maximum values of the smoothed A-line. By way of at least one embodiment example, the threshold may be computed, as follows:

Threshold=(mean+peak)/2, where "mean" is the average of the smoothed A-line and "peak" is the maximum value of the smoothed A-line. This threshold may be used to detect the most significant pulse corresponding to the lumen edge in a specific A-line. Any pulse above the threshold may be an edge pulse candidate in one or more embodiments. The largest pulse among all the candidates in terms of area under the pulse may be considered to be the maximum peak (or the "most significant pulse"). The second width of the highest peak may be defined as the one dimensional gradient signal along the A-line in the vicinity of the maximum peak, and may be used to identify the exact location of the lumen edge point in the smoothed A-line. The third width of the same peak may be defined along the A-line similar to the second width. However, for the third width, the gradient value will drop from its peak value to zero, which indicates the point that the value change stops and begins reversing its direction. By placing together all the lumen edge points thus detected from all the A-lines in one or more embodiments, the lumen edge for the vessel may be formed as a function of maximum peak locations vs. A-line indices.

As a further example, another approach to find the threshold is to find the average between the max peak and min peak as:

Threshold=(min+peak)/2.

A further alternative approach is to find the threshold based on the max peak as:

Threshold=(peak)×⅔.

The location of the highest peak of the one dimensional gradient signal along the A-line in the vicinity of the maximum peak may be used to identify the exact location of the lumen edge point in the smoothed A-line. Again, in one or more embodiments, the lumen edge data may contain or include artifact edge pixels.

In one or more embodiments, a guide wire artifact may be determined/detected and removed as discussed in U.S. Pat. App. No. 62/944,064, filed on Dec. 5, 2019, the disclosure of which is incorporated by reference herein in its entirety, and as discussed in U.S. patent application Ser. No. 17/098, 042, filed on Nov. 13, 2020, the disclosure of which is incorporated by reference herein in its entirety.

In one or more instances, a guide wire region may have a strong reflection, which corresponds to higher peak values. A guide wire region also may cover a larger range in terms of A-lines and often may have a strong reflection at the center A-lines. When a guide wire and stents both exist or are used in one or more embodiments, some stents struts may overlap with the guide wire, and the shadow regions may be extended by the stent(s). For those kind of conditions, identifying the guide wire correctly helps the further process to extract other stents.

One or more embodiments of the guide wire search process may be defined as or may include, as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety, one or more of the following: a) starting from the maximum peak values for all A-lines; b) growing the neighbor edge until either location or width jump finds a boundary point; c) continuing to grow around the boundary until the tissue only peak/edge pair is reached; d) growing back from the tissue only peak/edge pair until the end is reached; e) conducting the process on both directions; f) defining the range of the A-lines to include the tissue only peaks on both sides as the shadow range; g) calculating a shadow profile behind the tissue peaks to confirm the shadow does indeed exist; h) when the shadow is confirmed, the guide wire region is then confirmed; otherwise, iterate or repeat the process steps (a) to (h) with the next maximum peak value.

After the guide wire region has been identified, in one or more embodiments, the edge points may not be considered (and are, in one or more embodiments, preferably not considered) as the lumen edge and may be removed for stent detection step(s) that follow.

In one or more embodiments, stent detection may be performed as discussed in U.S. Pat. App. No. 62/944,064, filed on Dec. 5, 2019, the disclosure of which is incorporated by reference herein in its entirety, and as discussed in U.S.

patent application Ser. No. 17/098,042, filed on Nov. 13, 2020, the disclosure of which is incorporated by reference herein in its entirety. For example, stents may be detected by identifying stent strut candidates using one or more techniques, such as, but not limited to, edge jump stent detection, narrow peak width stent detection, etc. By way of at least one further example, stent strut candidates may be identified using location and peak width jumps. Confirmation and removal of the stent strut obstructed lumen edge points may share similar steps as done for sheath and/or guide wire detection and removal, but in a more iterative approach in one or more embodiments. First, in at least one embodiment, the major peak and edge profile for the whole lumen may be obtained with the guide wire removed. When there is/are stent(s) present in front of the lumen edge, the edge position jumps may indicate the possible stent candidates. For stents which are very close to the lumen edge either on one side or both sides, the stents and/or stent candidates may be identified by looking into the profile of the peak widths. The stent strut peaks tend to have small and equal peak widths compared to neighbor lumen peaks and corresponding edges.

In one or more embodiments, stent detection may be performed by merging and extending a stent region as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. Following the above lists or listing of stent strut candidates, in one or more embodiments, the search process may be conducted locally on each candidate to find the neighbor lumen edges on both sides of the stent strut. In at least one embodiment, the neighbor lumen edges are further extended until the connected peak and edge may no longer be confirmed to be a valid lumen edge. The covered region may be marked as confirmed edges. During one or more embodiments of the process, the candidates coming from different detection methods may have duplicates such that sets of candidates overlap. As such, the overlapping condition and the duplicates may be checked before proceeding on to the next step. Once all candidates are processed, the whole lumen edge circle may be marked as confirmed edges. Broken segments may be identified, and reasons for doing so are explained to at least confirm that the candidates and broken segments are all valid results.

In one or more embodiments, a shadow profile of the stent strut candidates may be calculated and/or a shadow pattern may be confirmed for an identified or found stent center location as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. For each stent, the interpolated lumen edge may exist between lumen edges on each of the sides, which is behind the detected peak and edge of the stent, in one or more embodiments. Based on the interpolated lumen peak position, the shadow accumulation profile may be calculated. In at least one embodiment, a normal shape of the shadow accumulation profile or shadow profile may be a single valley with a nadir (e.g., foot, base, lowest point, etc.) at, substantially at, or near the center of the valley. The minimum value location may be identified as the stent center, which corresponds to a middle of the stent strut that casted the shadow. There may exist some second reflection behind the stent shadow, which may distort the true shadow profile, in one or more embodiments. An additional process may be employed to remove the effects of such second reflections behind the stent shadow by identifying the narrow width peaks behind the interpolated lumen edge within the shadow and subtracting them from the original image.

In one or more embodiments, a lumen edge near the border may be extracted as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. As extra steps when processing each stent strut candidates, there may be one or more valid lumen edges that exist as secondary peaks behind the stent peak near the border region. Proper extraction and inclusion of the one or more valid lumen edges that exist as secondary peaks behind the stent peak improves the quality of the lumen edge results. This is one of the several unique aspects or features or improvements of the present disclosure compared to other methods because all such A-line results are often thrown away. The extraction of such a lumen edge may be based on the connectivity of the current lumen edge by searching a secondary peak outside of the major peak on the neighborhood A-line that already has been identified or that is identified as the non-lumen peak. The process may search on both sides of the stent neighborhood A-lines until no further peak is found in one or more embodiments.

In one or more embodiments, any missing portion of the lumen edge may be interpolated to fill in missing data as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. For example, for each confirmed stent location, any gap between or in the lumen edge may be filled using linear interpolation. Both lumen peak and edge information are kept and interpolated in one or more embodiments. After the process, the whole lumen circle may be processed and may form a closed circle-like curve for the lumen edge.

In one or more embodiments of embedded stent detection as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety, the peak curve may be similar and may be used to calculate a shadow accumulation profile or a shadow profile for the whole image. In one or more embodiments, finding an embedded stent and/or stent strut center may be based on the lumen peak curve or may be based on any other method or technique as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. For example, in one or more embodiments of embedded stent detection, a stent peak and/or edge behind the lumen edge may be found, a peak width and/or thickness may be calculated, the stent region may be merged and extended, an embedded stent(s) may be confirmed and extracted, and struts location information may be determined/identified, etc. Following the above discussed steps, for example, to identify and confirm the stent struts, valid embedded stents may be extracted and confirmed, with its location information (such as, but not limited to, strut center location) identified as well.

In one or more embodiments, the lumen edge may be output and/or the stent strut center location (and/or other stent strut location information) may be output as discussed, for example, in U.S. Pat. App. No. 62/944,064, filed on Dec. 5, 2019, the disclosure of which is incorporated by reference herein in its entirety, and in U.S. patent application Ser. No. 17/098,042, filed on Nov. 13, 2020, the disclosure of which is incorporated by reference herein in its entirety. A 1D smoothing filter may be applied to or used on the lumen edge results. The lumen edge and/or stent strut center location information (and/or other stent strut location information) may be output to a desired format, may be stored in a memory, may be printed, may be displayed on a display, etc.

One or more embodiments may detect the peaks and edges with three types of peak widths in each one-dimensional data (A-line) as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. In one or more embodiments, the maximum peak in each of the A-lines may be detected. The most significant pulse denotes the maximum peak and its associated front edge also named as "major peak/edge" in each of the A-lines in one or more embodiments. In one or more embodiments, a gradient of one-dimensional data (A-line) may be used to determine the edge location associated with each peak. In one or more embodiments, each peak may associate with three types of width: (1) a half-max width, (2) max gradient width, and (3) minimal value width, which defines the peak range on the A-line. The half-max width, which is the first width, may be used to test connectivity between neighbor peaks. The max gradient width, which is the second width, may be used to indicate a thickness of the object. The minimal value width, which is the third width, may be used to define the peak range. In one or more embodiments, other peaks may exist outside of a current peak range. One or more embodiments may group connected peaks on different neighbor A-lines together to form geometrically separate objects in 2D space.

One or more embodiments may distinguish the lumen edge peak from the guide wire and stent struts. For example, in one or more embodiments, disconnected major peaks in neighbor A-lines may indicate separate objects, such as a lumen edge peak and a guide wire or stent strut(s). The peak location connectivity may exist in a case where the stent strut peak edge is very close to the lumen edge in neighbor A-lines. In such cases, the lumen and stent may be separated by the jump of the peak widths. In one or more embodiments, peak widths of stent strut(s) are small and near constant, including the first, second, and third widths, because of a shadow behind the stent strut(s). Therefore, both peak location and the peak widths' values are used to separate the objects, such as a lumen edge peak and a guide wire or stent strut(s).

One or more embodiments of the present disclosure may grow major peaks into neighbor A-lines around the boundary region between the lumen and the stent strut(s) or guide wire. Multiple peaks may exist when peaks from a neighbor A-line grow by searching a local peak which is outside the major peak on the current A-line. Both a lumen edge region and stent strut objects may be grown into more complete objects that leads to an improved, optimal, and/or correct decision of the boundary between the lumen and the stent strut(s) or guide wire (which may be useful in one or more situations, including, but not limited to, some challenging cases).

One or more embodiments of the present disclosure may calculate the shadow accumulation profile (or shadow profile) locally based on the interpolation of lumen peaks on both sides of the guide wire and/or stent strut(s). In one or more embodiments, the interpolation may happen on both sides of the guidewire and the stent struts. Interpolation of lumen edge peaks may be used to calculate the shadow profile because starting points for the accumulation calculation may be critical and/or may substantially improve the accuracy in one or more embodiments. A shape of the shadow profile may be used to confirm or ensure that the area includes or contains a valid shadow. As aforementioned, a single valley shadow may be used to find a center location for a stent strut(s).

One or more embodiments may process stent candidates iteratively to complete the lumen profile for the whole image. A guide wire region may be processed first, and then each stent candidate may be processed locally for better accuracy. Both lumen peak and lumen edge curves may be generated to confirm the results.

One or more embodiments of the present disclosure may use a global lumen peak curve to calculate the shadow profile and to detect embedded stent(s). An interpolated peak curve may be used to calculate the global shadow profile in one or more embodiments, and/or the global shadow profile may be used to identify the embedded stent strut(s). In one or more embodiments, embedded stent strut(s) may be extracted using a secondary peak width pattern.

Additionally or alternatively, in one or more embodiments, a principal component analysis method and/or a regional covariance descriptor(s) may be used to detect objects, such as stents. Cross-correlation among neighboring images may be used to improve lumen edge detection result(s). One or more embodiments may employ segmentation based image processing and/or gradient based edge detection to improve detection result(s).

As discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety, the OCT image in polar coordinates (e.g., of a stented vessel) may be displayed vertically (rather than, or in addition to, horizontally), and/or may be displayed with a corresponding OCT image in Cartesian Coordinates using at least one apparatus or system for performing lumen, stent, and/or artifacts detection techniques in accordance with one or more aspects of the present disclosure.

In accordance with at least one aspect of the present disclosure and as aforementioned, one or more additional methods for lumen, stent, and/or artifacts detection of OCT images are provided herein, or may be used with one or more of the features or aspects of the present disclosure, and are discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety.

Placing together all the lumen edge points thus detected from all the A-lines forms the lumen edge (in one or more embodiments, the lumen edge data may contain or include artifact edge pixels) for the vessel as a function of maximum peak locations vs. A-line indices.

In one or more method embodiments, edge points corresponding to large the falling and rising gradient ratio (FRGR) and small sized pulses may be removed as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety. The falling and rising gradient ratio may be used as an indicator of the stent strut and guidewire presence if the detected lumen edge and its corresponding falling rising gradient ratio are plotted together as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety.

In one or more embodiments, one may use either the pulse width or the area under the 1D signal pulse as the measure of the signal pulse size as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety.

Using the noticeable differences of the falling raising gradient ratio and the differences in a size of the A-line pulses, the artifact region locations corresponding to the guidewire and stent struts in the detected lumen edge may be identified using simple thresholding where the threshold may be set, for example, as:

$$PulseSizeThreshold = mean - sigma \times k1$$

Or $$FRGRThreshold = mean + sigma \times k2,$$

where "mean" and "sigma" are the mean and standard deviation of the corresponding signal, and k1, k2 are empirical parameters preferably chosen, but not limited to, between 1 to 2.

An alternative approach to calculate the thresholds may be:

$$PulseSizeThreshold = mean + (peak - mean)/3$$

Or $$FRGRThreshold = mean + (peak - mean)/3$$

Furthermore, as another alternative, the thresholds may also be calculated as:

$$PulseSizeThreshold = peak - (peak - mean)/2$$

Or $$FRGRThreshold = peak - (peak - mean)/2$$

Preferably, in one or more embodiments, these identified edge points are not considered as the lumen edge and are not used for lumen parameter calculation.

One advantage of using one dimensional A-line signal processing for lumen edge detection is that there may be a multi-peak pattern of these boundary regions from the A-line signal because both stents and lumen edge peaks exist in the A-line signal. For example, as discussed in U.S. patent application Ser. No. 16/414,222, filed on May 16, 2019, the entire disclosure of which is incorporated by reference herein in its entirety, and as discussed in U.S. Pat. Pub. No. 2019/0374109, which was published on Dec. 12, 2019, the disclosure of which is incorporated by reference herein in its entirety, the boundary region may produce clustered multi-peak pulses in the A-line signal. Multi-peak pulses may be detected using the same threshold used in the maximum peak detection step as discussed above, and is not repeated herein as a result. If a falling edge of a peak rises again before the falling edge falls below the threshold, a multi-peak pulse is considered to be identified in at least one embodiment. Preferably, if a pulse is detected as a multi-peak pulse, the lumen edge data from that A-line may be considered as the boundary region of the stent struts and guidewire and removed from lumen edge detection. In one or more embodiments, multi-peaks not in the boundary region may be retained, and are preferably retained in one or more embodiments.

Even if a falling edge of a peak falls below the threshold and then raises again to form another peak, it may still be considered as a multi-peak pulse. The correct identification of the lumen edge may then rely on the major peak detection and the size of the front peak in at least one embodiment. If the front peak is identified as the artifacts, such as, but not limited to, a stent or guidewire, the second peak may be the lumen edge. There may be small vessel branch presented in the tissue underneath the vessel wall, which may end up manifesting as two separate peaks in a single A-line in a similar manner in one or more embodiments. In such a case, the front peak without the narrow width may be the lumen edge. At least one way to distinguish multi-peak pulses between the valid lumen edge versus an influence of one or more artifacts is determining whether they are located within the boundary regions. Therefore, the multi-peak cases may be further classified into the non-boundary region and boundary region cases, and they may be removed from the detected lumen edge only in the boundary regions.

By way of another example and alternative to the aforementioned example, horizontal gradients may be used to identify and remove the lumen edge data corresponding to the boundary region between the soft tissue and narrow artifacts. As discussed in U.S. patent application Ser. No. 16/414,222, filed on May 16, 2019, the entire disclosure of which is incorporated by reference herein in its entirety, and as discussed in U.S. Pat. Pub. No. 2019/0374109, which was published on Dec. 12, 2019, the disclosure of which is incorporated by reference herein in its entirety, a gradient across the A-lines may display a pattern of many shadows (which may include one or more artifact shadows) caused by the light blocking artifacts.

For each detected lumen edge point, the average values of across the A-lines gradient below the edge point may be computed as discussed in U.S. patent application Ser. No. 16/414,222, filed on May 16, 2019, the entire disclosure of which is incorporated by reference herein in its entirety, and as discussed in U.S. Pat. Pub. No. 2019/0374109, which was published on Dec. 12, 2019, the disclosure of which is incorporated by reference herein in its entirety. These average values reflect the locations of the shadows caused by the light blocking artifacts. Given the directional property of the gradient across the A-lines, the bright to dark edge produces a rising peak while the dark to bright edge produces a falling peak. For each dark shadow produced by the stent strut, the shadow is bordered by a rising peak at one side and by a falling edge at the other side.

In one or more method embodiments, edge points corresponding to multi-pulse A-lines may be removed as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety. For example, lumen edge data corresponding to a ghost signal or ghost signals produced (e.g., from reflection(s) of stent(s), any signal(s) other than the targeted signal, a luminance signal, etc.) may be identified and removed by detecting multiple pulses.

When there is strong reflection caused by the stent struts or guidewire, there may be a ghost signal or signals in the A-line signal due to a detected multipath signal. As another advantage of using one dimensional A-line signal processing for lumen edge detection, this ghost signal (or signals) manifests itself as an additional pulse signal in the A-line signal as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety. For example, an A-line plot may show two peaks in which the right peak corresponds to the ghost signal and the left peak corresponds to a stent strut as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety. Peaks of all significant pulses in the A-line signal may be determined.

Given that the most likely sources of strong reflection are stent struts and guidewire, the detected lumen edge points corresponding to the A-lines with a ghost signal (or signals) are preferably excluded from the parameter calculation for the lumen.

In one or more method embodiments, a lumen edge may be formed as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety. For example, after removing all the artifacts from the detected lumen edge (e.g., edge points with a narrow pulse width (which correspond to edge points from guide wire(s) and stent(s)) may be removed; edge points with large FRGR (which correspond to edge points from weak stent(s)) may be removed; edge points with separated multiple large pulses (which correspond to stents with a reflection image) may be removed; edge points with clustered multiple pulses (which correspond to the boundary of soft tissue and the stent(s)) may be removed; etc.), the gaps in the lumen edge may be filled using simple interpolation (e.g., linear interpolation) using the neighboring edge points. One embodiment example for doing this is to have the lumen edge undergo median filtering.

In one or more method embodiments, a lumen edge may be smoothed as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety. For example, the lumen edge may undergo low pass filtering. In one or more embodiments, some simple median filtering and low pass filtering may be applied to lumen edge (edge locations vs. A-line pixels) to smooth and polish the final lumen edge.

In one or more method embodiments, a lumen edge may be converted into Cartesian coordinates as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety.

At least one embodiment of a method for detecting lumen edges and artifacts may be summarized as follows: The OCT image in polar coordinates may be filtered using a two dimensional Gaussian filter to reduce the noise in the image. The separate gradient in vertical and horizontal directions may be computed using the Sobel filters from the filtered image. For each A-line, one-dimensional filtering is applied to further smooth the A-line signal and remove the signal offset. The gradient along the A-line direction may be further smoothed using a low pass filter. For each A-line, all the significant pulses in the A-line signal may be found, and the most significant pulse and its position may be determined as the lumen data, based on the detection threshold and the pulse size using either pulse width or area under the pulse. The falling rising gradient ratio for the most significant pulse (lumen data) in each A-line may be computed. The lumen data may be removed, and a gap may be identified if the falling rising gradient ration is larger than the threshold value. The lumen data may be removed, and a gap may be identified if the pulse size is smaller than the threshold pulse size. The lumen data may be removed, and a gap may be identified if the detected pulses are multi-peak pulse(s) or where an artifact region detected from the previous step is bordered by the rising and falling peaks of the gradient across A-lines. The lumen data may be removed, and a gap may be identified if there is more than one comparable pulse in the A-line signal. Thereafter, the gaps are filled in the lumen edge using linear interpolation. Median filtering and/or low pass filtering may be applied to the lumen edge. The lumen edge may be converted into Cartesian coordinates for display.

One or more embodiments of a method(s) for detecting lumen and artifacts may be performed with or without the filtering of the lumen edge. For example, median filtering and/or low pass filtering the lumen edge is optional in one or more embodiments. In one or more embodiments, alternative methods for smoothing the lumen edge may be used in place of the median filtering and/or low pass filtering of the lumen edge.

One or more alternative embodiments of a method(s) for detecting lumen and artifacts may be performed by detecting a signal edge pixel from each one-dimensional data (A-line). A-lines with a significant pulse peak may be selected. Each one-dimensional data (A-line) may have its own detection threshold for pulse detection, and the respective threshold may change among different A-lines in an image. A gradient of one-dimensional data (A-line) may be used to further determine the lumen edge pixel location.

One or more alternative embodiments of a method(s) for detecting lumen and artifacts may be performed by introducing an FRGR to distinguish the edges of the target or object (e.g., soft tissue), guide wire(s), stent(s) and/or any other component being used in the procedure. The pulse size of the one dimension data is introduced to distinguish the target or object (e.g., soft tissue), guide wire(s), stent(s), and/or any other component or artifact(s) related to the procedure(s).

One or more alternative embodiments of a method(s) for detecting lumen and artifacts may be performed by identifying the boundary region between the target or object (e.g., soft tissue) and the stent strut(s), guide wire(s), or other artifacts. Multiple peaks in an A-line may represent a blurred boundary between the target or object (e.g., soft tissue) and the stent strut(s), guide wire(s), or other artifacts. The multi-peaks may be used as a signature to identify the boundary.

One or more alternative embodiments of a method(s) for detecting lumen and artifacts may be performed by identifying the boundary region between the target or object (e.g., soft tissue) and narrow stent strut(s). Variation of the gradient along the horizontal direction (across the A-lines) in the region behind the detected lumen edge may be utilized to improve the determination of the location of the artifact region.

One or more alternative embodiments of a method(s) for detecting lumen and artifacts may be performed by identifying ghost signal(s) produced from reflection of stent(s). A ghost signal may cause multiple peaks in an A-line signal. One way to handle this is to remove the area where the multiple pulses/peaks are detected.

As aforementioned for one or more embodiments of a method(s) for detecting lumen and artifacts, interpolation may be used to sample the data that is removed, and to form the lumen edge. The final edge may be smoothed or polished using filters as aforementioned.

A computer, such as the console or computer 1200, 1200', may perform any of the steps, processes, and/or techniques discussed herein for any apparatus and/or system being manufactured or used, including, but not limited to, apparatus or system 100, apparatus or system 100', apparatus or system 100", apparatus or system 100''', any of the embodiments shown in FIGS. 3A-3J, any other apparatus or system discussed herein, etc.

Figure 11:
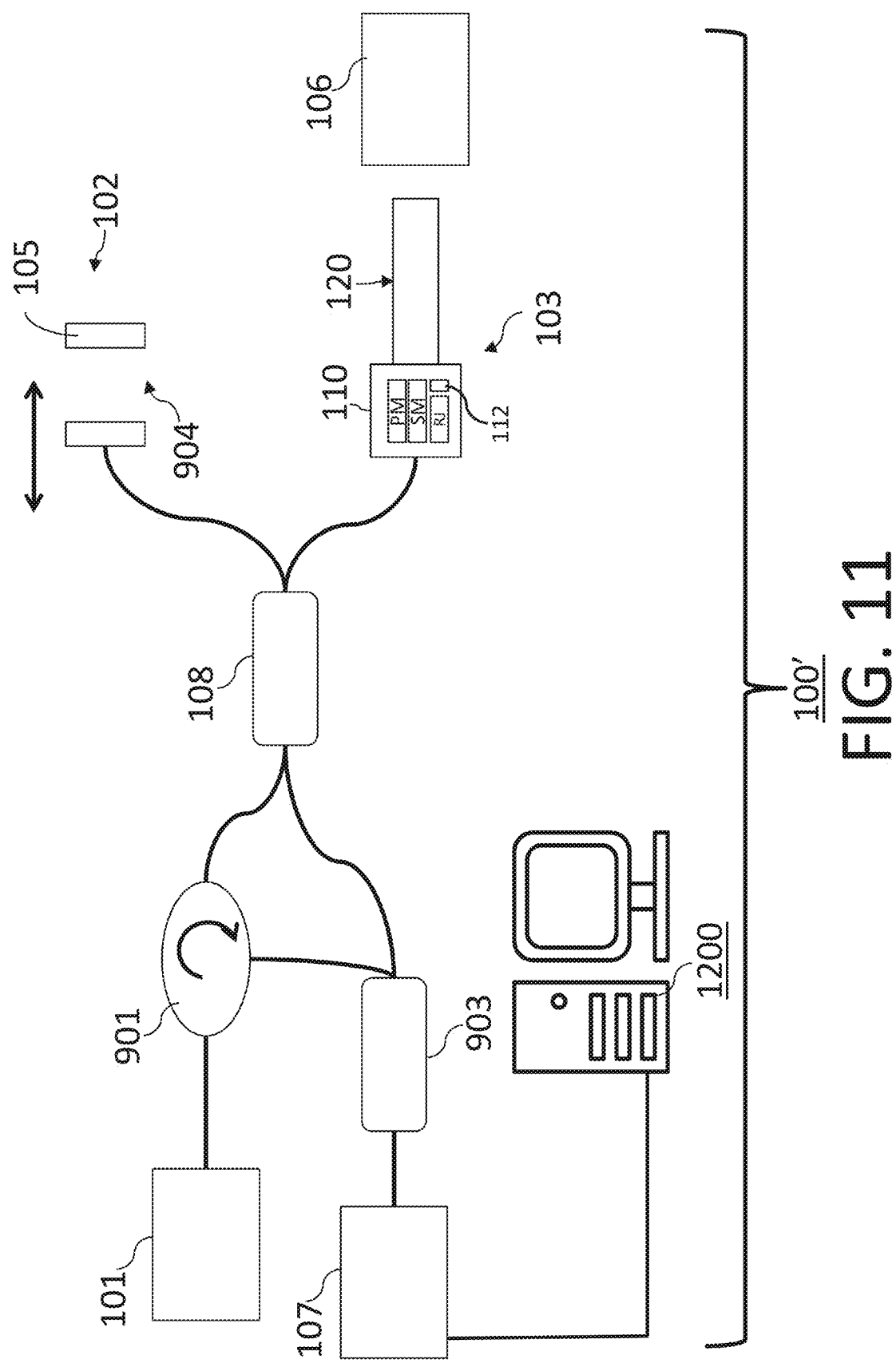
FIG. 11 is a diagram showing an embodiment of at least another system which can utilize one or more engagement and/or disengagement status determination and/or engagement and/or disengagement guidance techniques in accordance with one or more aspects of the present disclosure.

In accordance with one or more further aspects of the present disclosure, bench top systems may be utilized with the techniques, such as, but not limited to, the detecting and guiding optical connection techniques, disclosed herein. FIG. 11 shows an example of a system that can utilize the detecting and guiding techniques for a bench-top such as for ophthalmic applications. A light from a light source 101 delivers and splits into a reference arm 102 and a sample arm 103 with a deflecting (or deflection) section 108. A reference beam goes through a length adjustment section 904 (which is optional in one or more embodiments) and is reflected from a reference mirror (such as reference mirror or reference reflection 105 shown in FIG. 1) in the reference arm 102 while a sample beam is reflected or scattered from a sample, target or object 106 in the sample arm 103 (e.g., via the PIU 110 and the catheter 120). In one embodiment, both beams combine at the deflecting/deflection section 108 and generate interference patterns. In one or more embodiments, the beams go to the combiner 903, and the combiner 903 combines both beams via the circulator 901 and the deflecting section 108. The combined beams preferably are delivered to one or more detectors (such as the one or more detectors 107). The output of the beam splitter (see e.g., beam splitter 104 in FIG. 1), the deflecting section 1o8, and/or an interferometer is continuously acquired with one or more detectors, such as the one or more detectors 107. The electrical analog signals are converted to the digital signals to analyze them with a computer, such as, but not limited to, the computer 1200 (see FIG. 1; also shown in FIGS. 11-13 and 15 discussed further below), the computer 1200' (see e.g., FIG. 16 discussed further below), etc.

Figure 12:
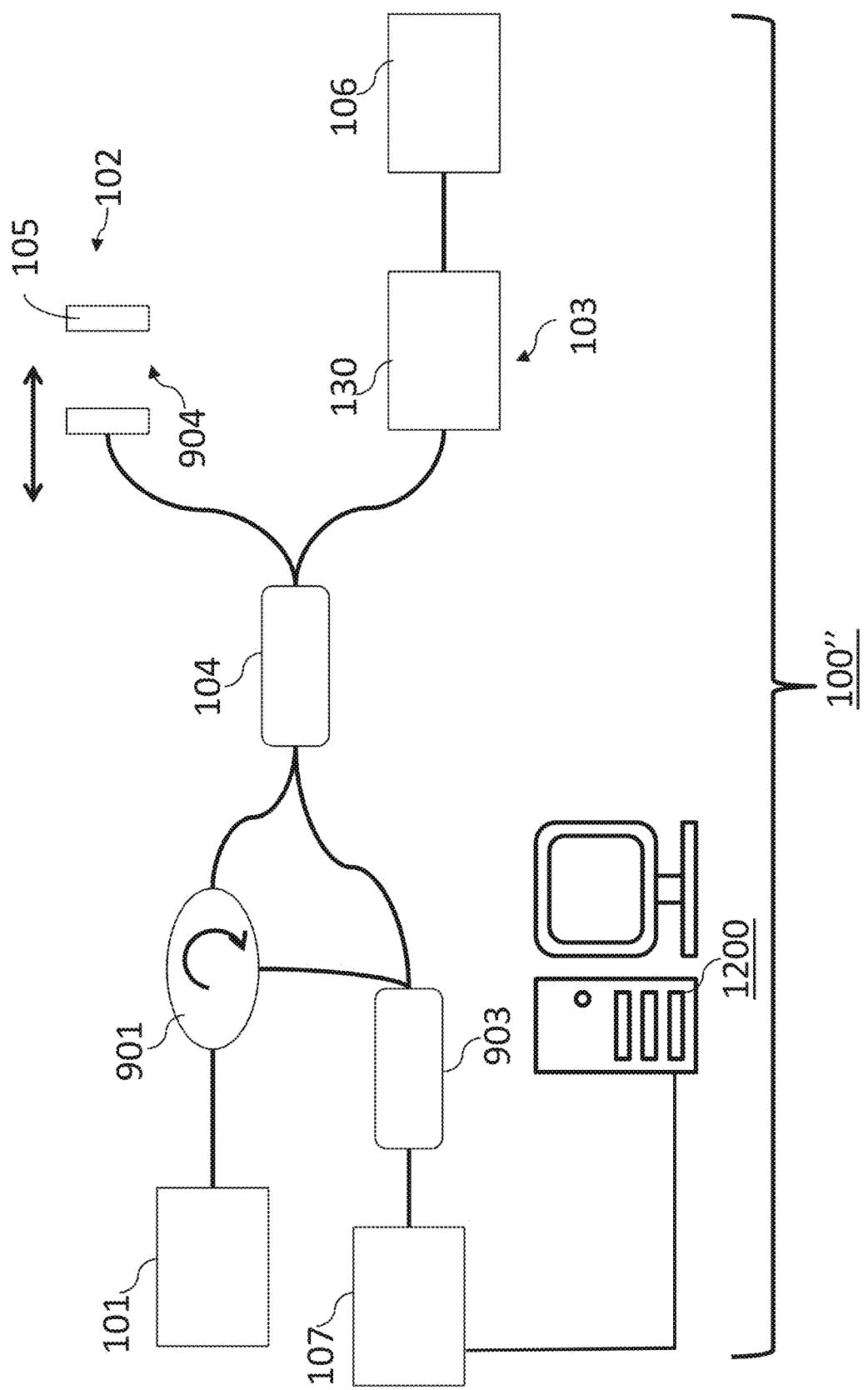
FIG. 12 is a diagram showing an embodiment of at least a further system which can utilize one or more engagement and/or disengagement status determination and/or engagement and/or disengagement guidance techniques in accordance with one or more aspects of the present disclosure.

In one or more embodiments, the sample arm 103 may include a phase shift unit 103 for a bench top system(s) as shown in system 100" in FIG. 12. The sample 106 may be located at the place of the mirror 105 used with the phase shift unit 130 (e.g., as shown in FIG. 1). A light from a light source 101 delivers and splits into a reference arm 102 and a sample arm 103 with a splitter 104. A reference beam goes through a length adjustment section 904 and is reflected from a reference mirror (such as reference mirror 105 shown in FIGS. 11-13) in the reference arm 102 while a sample beam is reflected or scattered from a sample, target and/or object 106 through a phase shift unit (such as the phase shift unit 130) in the sample arm 103. In one embodiment, both beams combine at the splitter 104 and generate interference patterns. In one or more embodiments, the beams go to the combiner 903, and the combiner 903 combines both beams via the circulator 901 and the splitter 104, and the combined beams are delivered to one or more detectors (such as the one or more detectors 107). The output of the beam splitter 104 and/or an interferometer is continuously acquired with one or more detectors, such as the one or more detectors 107. The electrical analog signals are converted to the digital signals to analyze them with a computer.

There are many ways to compute rotation, intensity, or any other measurement discussed herein, and/or to control and/or manufacture an MMOCT device/apparatus, system and/or storage medium, digital as well as analog. In at least one embodiment, a computer, such as the console or computer 1200, 1200', may be dedicated to control and/or use OCT devices, systems, methods and/or storage mediums for use therewith described herein.

Figure 13:
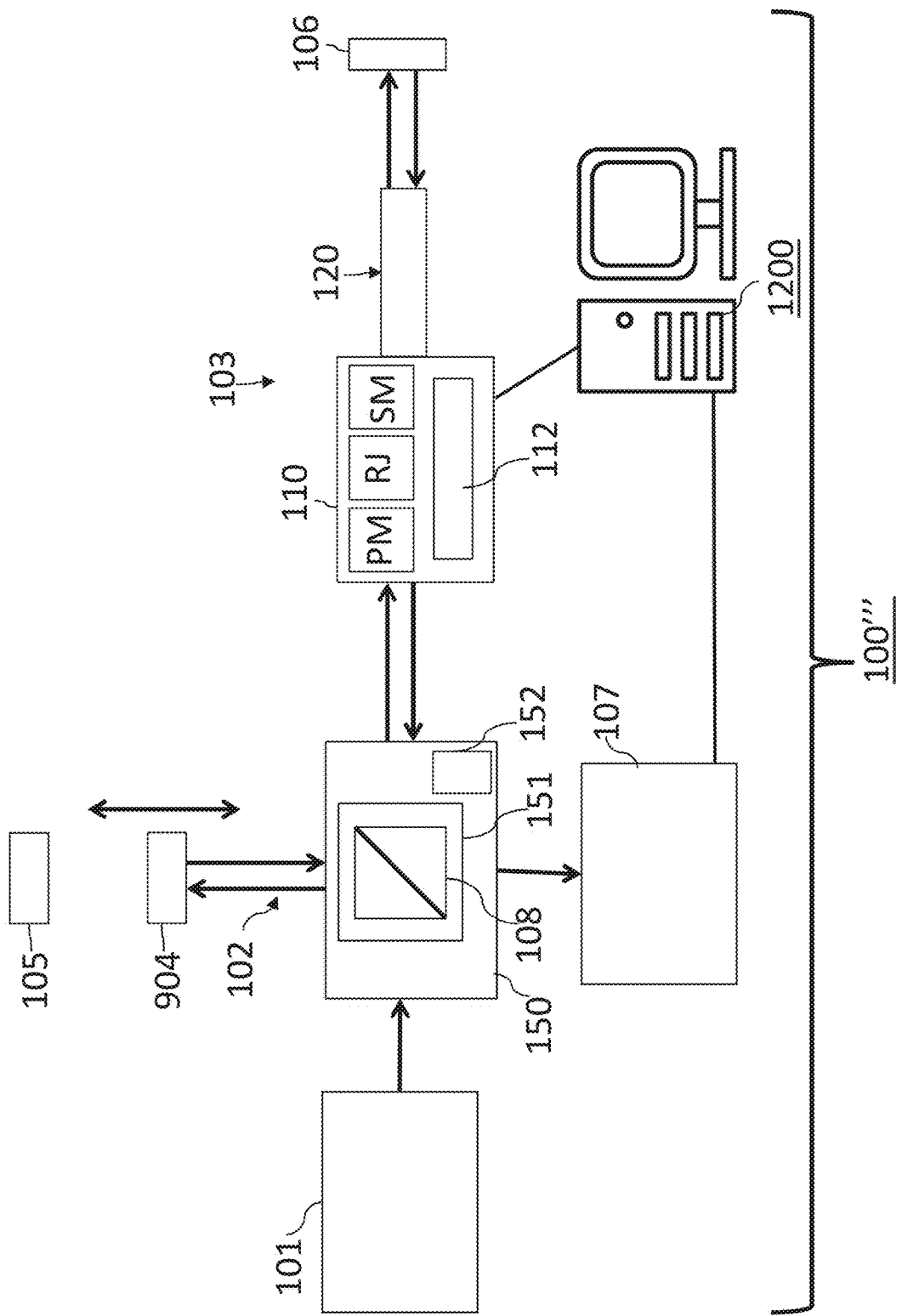
FIG. 13 is a diagram showing an embodiment of at least yet a further system which can utilize one or more engagement and/or disengagement status determination and/or engagement and/or disengagement guidance techniques in accordance with one or more aspects of the present disclosure.

In accordance with one or more further aspects of the present disclosure, one or more other systems may be utilized with the lumen edge and artifact(s) detection OCT techniques disclosed herein. FIG. 13 shows an example of a system 100''' that may utilize the detecting and guiding techniques such as for ophthalmic applications. A light from a light source 101 delivers and splits into a reference arm 102 and a sample arm 103 with a deflecting section 108 (e.g., a beam splitter or other deflecting or deflected section discussed herein) located inside of an OCT imaging engine 150, which may also include an OCT interferometer 151 (which may house or include the deflecting section 108) and a swept source engine 152 in one or more embodiments. A reference beam may pass through a length adjustment section 904, which may operate to change the distance of a reference mirror (such as reference mirror or reference reflection 105; also shown in FIG. 1) and is reflected from the reference reflection 105 in the reference arm 102 while a sample beam is reflected or scattered from a sample, target or object 106 in the sample arm 103. In one embodiment, both beams combine at the deflecting section 108 and generate interference patterns. In one or more embodiments, the combined beams are delivered to one or more detectors. The output of the interferometer 151 is continuously acquired with one or more detectors, such as the one or more detectors 107. The electrical analog signals are converted to the digital signals to analyze them with a computer, such as, but not limited to, the computer 1200 (see e.g., FIG. 1; also shown in FIGS. 11-13 and 15 discussed further below), the computer 1200' (see e.g., FIG. 16 discussed further below), etc. In one or more embodiments, the sample arm 103 includes the PIU 110 and the catheter 120 so that the sample beam is reflected or scattered from the sample, target or object 106 as discussed herein. In one or more embodiments, the PIU 110 may include one or more motors to control the pullback operation of the catheter 120 (or one or more components thereof) and/or to control the rotation or spin of the catheter 120 (or one or more components thereof). For example, the PIU 110 may include a pullback motor (PM) and a spin motor (SM), and/or may include a motion control unit 112 that operates to perform the pullback and/or rotation features using the pullback motor PM and/or the spin motor SM. As discussed herein, the PIU 110 may include a rotary junction (e.g., rotary junction RJ as shown in FIGS. 11 and 13). The rotary junction RJ may be connected to the spin motor SM so that the catheter 120 may obtain one or more views or images of the sample 106. The computer 1200 (or the computer 1200') may be used to control one or more of the pullback motor PM, the spin motor SM and/or the motion control unit 112. An OCT system may include one or more of the OCT engine 150, a computer (e.g., the computer 1200, the computer 1200', etc.), the PIU 110, the catheter 120, a monitor, etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

Unless otherwise discussed herein, like numerals indicate like elements. For example, while variations or differences exist between the systems/apparatuses, such as, but not limited to, the system 100, the system 100', the system 100", the system 100''', the systems/apparatuses of FIGS. 3A-3J, etc. (e.g., differences between the position(s) of the reference reflection 105 (and/or reference arm 102) depending on the OCT system or method being used), one or more features thereof may be the same or similar to each other, such as, but not limited to, the light source 101, the deflecting section 108 or other component(s) thereof (e.g., the console 1200, the console 1200', etc.). Those skilled in the art will appreciate that the light source 101, the at least one detector 107 and/or one or more other elements of the system 100, may operate in the same or similar fashion to those like-numbered elements of one or more other systems, such as, but not limited to, the system 100', the system 100", the system 100''', etc. as discussed herein. Those skilled in the art will appreciate that alternative embodiments of the system 100, the system 100', the system 100", the system 100''', the systems/apparatuses of FIGS. 3A-3J, and/or one or more like-numbered elements of one of such systems, while having other variations as discussed herein, may operate in the same or similar fashion to the like-numbered elements of any of the other systems (or component(s) thereof) discussed herein. Indeed, while certain differences exist between the system 100, the system 100', the system 100" and the system 100''', the systems/apparatuses of FIGS. 3A-3J, etc. as discussed herein, there are similarities between the apparatuses/systems discussed herein. Likewise, while the console or computer 1200 may be used in one or more systems (e.g., the system 100, the system 100', the system 100", the system 100''', the systems/apparatuses of FIGS. 3A-3J, etc.), one or more other consoles or computers, such as the console or computer 1200', may be used additionally or alternatively.

Figure 14:
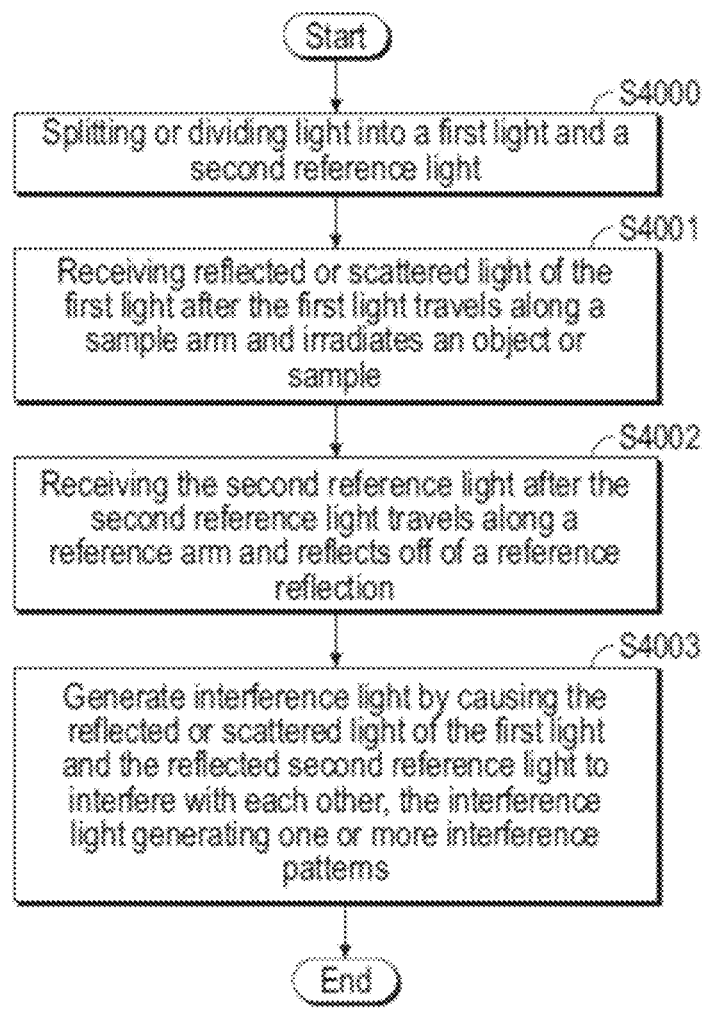
FIG. 14 is a flow diagram illustrating at least one method embodiment of performing an imaging feature, function or technique that may be used with one or more engagement and/or disengagement status determination and/or engagement and/or disengagement guidance techniques in accordance with one or more aspects of the present disclosure.

In accordance with one or more aspects of the present disclosure, one or more methods for detecting and guiding optical connections are provided herein, and one or more methods for performing imaging are provided herein. FIG. 14 illustrates a flow chart of at least one embodiment of a method for performing imaging. Preferably, the method(s) may include one or more of the following: (i) splitting or dividing light into a first light and a second reference light (see step S4000 in FIG. 14); (ii) receiving reflected or scattered light of the first light after the first light travels along a sample arm and irradiates an object or a sample (see step S4001 in FIG. 14); (iii) receiving the second reference light after the second reference light travels along a reference arm and reflects off of a reference reflection (see step S4002 in FIG. 14); and (iv) generating interference light by causing the reflected or scattered light of the first light and the reflected second reference light to interfere with each other (for example, by combining or recombining and then interfering, by interfering, etc.), the interference light generating one or more interference patterns (see step S4003 in FIG. 14). One or more methods may further include using low frequency monitors to update or control high frequency content to improve image quality. For example, one or more embodiments may use balanced detection, polarization diversity, automated polarization control, etc. to achieve improved image quality. In one or more embodiments, an imaging probe may be connected to one or more systems (e.g., the system 100, the system 100', the system 100", the devices, apparatuses or systems of FIGS. 3A-3J, any other system or apparatus discussed herein, etc.) with a connection member or interface module. For example, when the connection member or interface module is a rotary junction for an imaging probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the imaging probe may be separate from the detection portion of the imaging probe. For example, in one or more applications, a probe may refer to the illumination assembly, which includes an illumination fiber (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: a detection fiber, a detector (e.g., the one or more detectors 107, a spectrometer, etc.), the computer 1200, the computer 1200', etc. The detection fibers may surround the illumination fiber, and the detection fibers may or may not be covered by a grating, a spacer, a lens, an end of a probe or catheter, etc.

There are many ways to compute power and/or detect lumen edge(s) and artifact(s), and/or detect and/or guide optical connections/disconnections, digital as well as analog. In at least one embodiment, a computer, such as the console or computer 1200, 1200', may be dedicated to the control and the monitoring of the OCT devices, systems, methods and/or storage mediums described herein.

The electric signals used for imaging may be sent to one or more processors, such as, but not limited to, a computer 1200 (see e.g., FIGS. 1, 11-13, and 15), a computer 1200' (see e.g., FIG. 16), etc. as discussed further below, via cable(s) or wire(s), such as, but not limited to, the cable(s) or wire(s) 113 (see FIG. 15).

Figure 15:
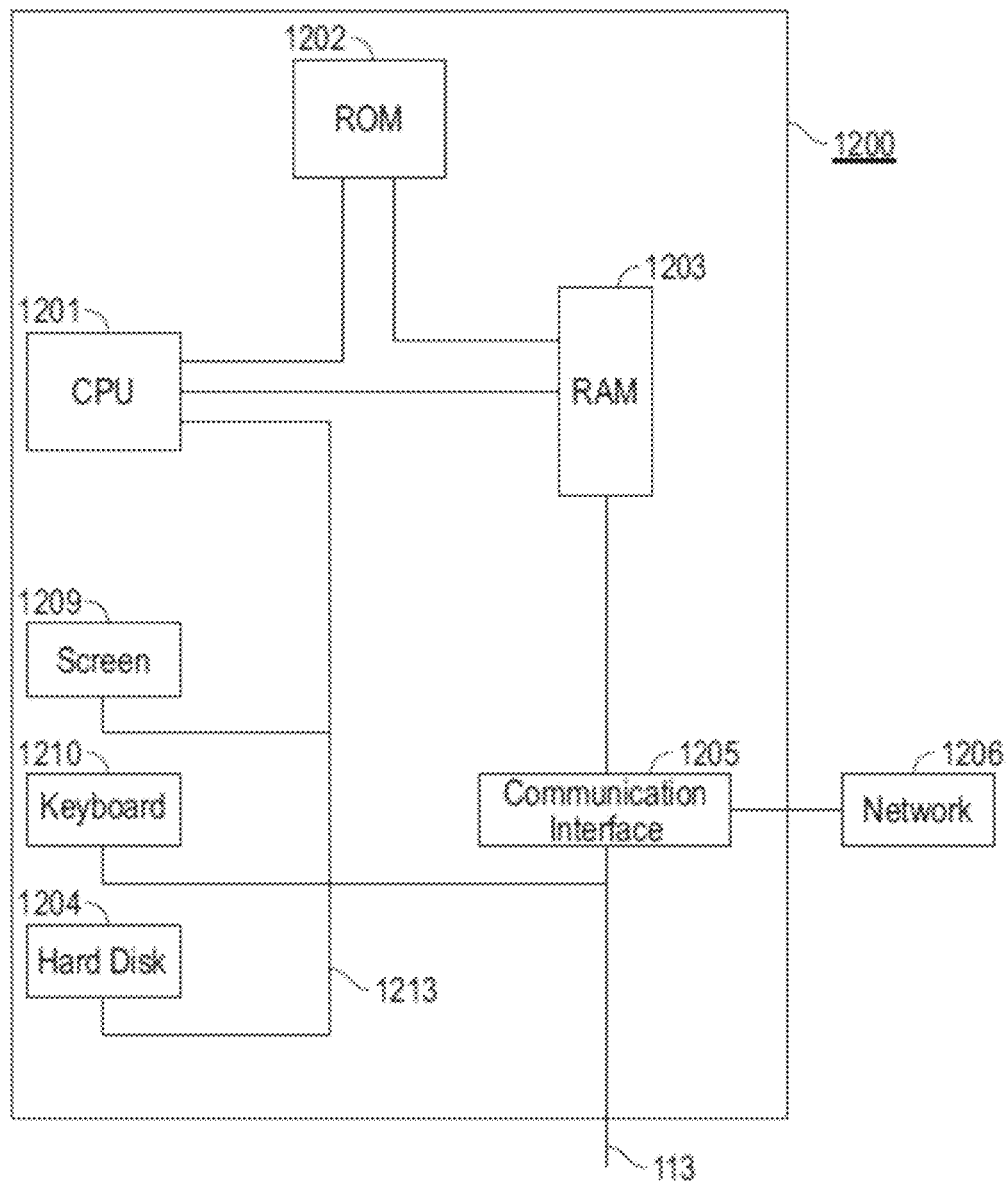
FIG. 15 shows a schematic diagram of an embodiment of a computer that may be used with one or more embodiments of at least one apparatus, system, method, and/or storage medium, including, but not limited to, for performing one or more engagement and/or disengagement status determination and/or engagement and/or disengagement guidance techniques, in accordance with one or more aspects of the present disclosure.

Various components of a computer system 1200 (see e.g., the console or computer 1200 as shown in FIGS. 1 and 11-13) are provided in FIG. 15. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 15). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a FORJ or a device or system using same, such as, but not limited to, the system 100, the system 100', the system 100'', the system 100''', and/or the systems/apparatuses of FIGS. 3A-3J, discussed herein above, via one or more lines 1213), and one or more other computer systems 1200 may include one or more combinations of the other aforementioned components. The CPU 1201 is configured to read and perform computer-executable instructions stored in a storage medium. The computer-executable instructions may include those for the performance of the methods and/or calculations described herein. The computer system 1200 may include one or more additional processors in addition to CPU 1201, and such processors, including the CPU 1201, may be used for controlling and/or manufacturing a device, system or storage medium for use with same or for use with any lumen detection, stent(s) detection, artifact(s) detection, and/or detecting and/or guiding optical connections technique(s) discussed herein. The system 1200 may further include one or more processors connected via a network connection (e.g., via network 1206). The CPU 1201 and any additional processor being used by the system 1200 may be located in the same telecom network or in different telecom networks (e.g., performing, manufacturing, controlling and/or using technique(s) may be controlled remotely).

Figure 16:
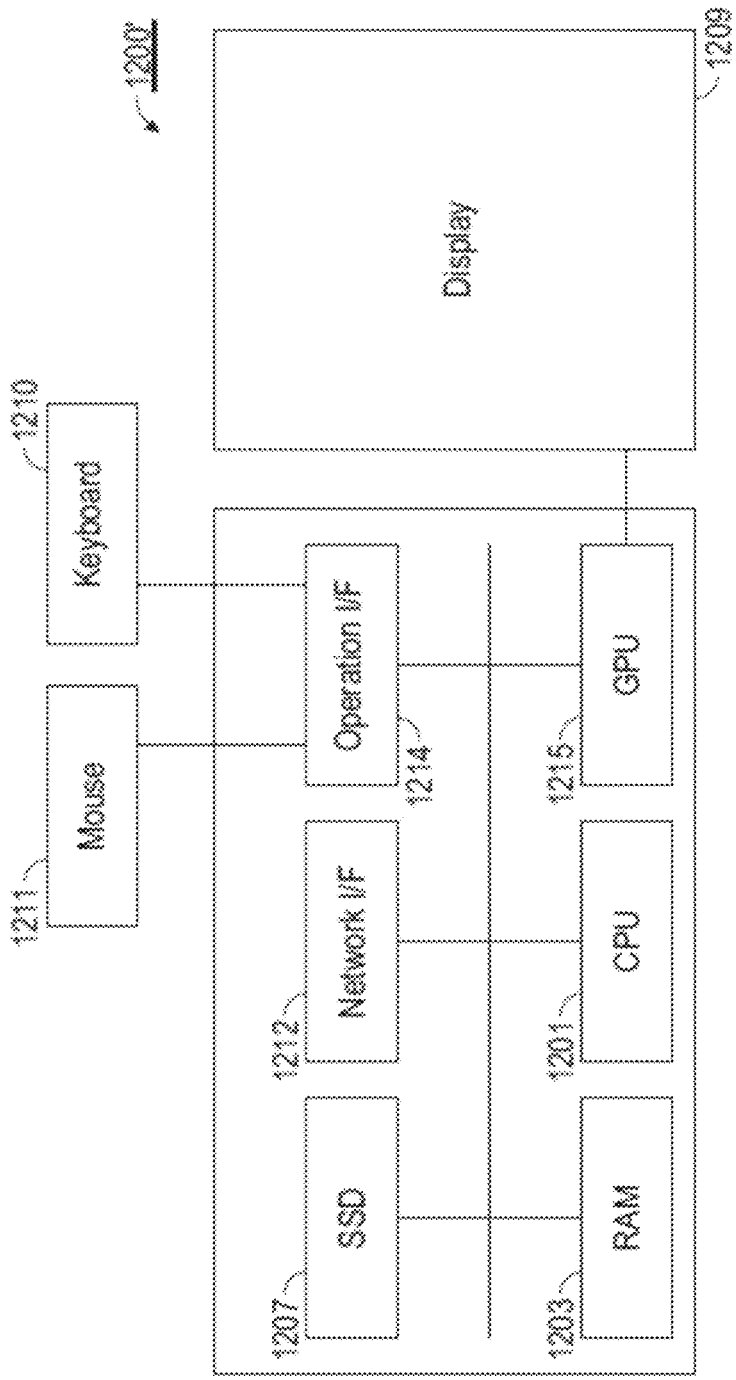
FIG. 16 shows a schematic diagram of another embodiment of a computer that may be used with one or more embodiments of at least one apparatus, system, method, and/or storage medium, including, but not limited to, for performing one or more engagement and/or disengagement status determination and/or engagement and/or disengagement guidance techniques, in accordance with one or more aspects of the present disclosure.

The I/O or communication interface 1205 provides communication interfaces to input and output devices, which may include the light source 101, a RJ, a PM, an SM, unit 150, unit 112, a microphone, a communication cable and a network (either wired or wireless), a keyboard 1210, a mouse (see e.g., the mouse 1211 as shown in FIG. 16), a touch screen or screen 1209, a light pen and so on. The Monitor interface or screen 1209 provides communication interfaces thereto.

Any methods and/or data of the present disclosure, such as the methods for using and/or manufacturing a device, system or storage medium for use with same and/or method(s) for detecting lumen edge(s), stent(s), and/or artifact(s), including in OCT image(s), and/or for detecting and/or guiding optical connections, as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-Ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 16), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined, limited, or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, devices, systems, and computer-readable storage mediums related to the processors, such as, but not limited to, the processor of the aforementioned computer 1200, the processor of computer 1200', etc., as described above may be achieved utilizing suitable hardware, such as that illustrated in the figures. Functionality of one or more aspects of the present disclosure may be achieved utilizing suitable hardware, such as that illustrated in FIG. 15. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 15 or FIG. 16) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 16. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid-state drive (SSD) 1207. Preferably, the computer or console 1200' includes a display 1209. The computer 1200' may connect with a rotary junction (e.g., RJ of FIG. 11, RJ of FIG. 13, etc.), the motor PM, the motor SM, and/or one or more other components of a system (e.g., the system 100, the system 100', the system 100", the system 100''', the systems/apparatuses of FIGS. 3A-3J, etc.) via the operation interface 1214 or the network interface 1212. A computer, such as the computer 1200, 1200', may include the RJ, PM and/or the SM in one or more embodiments. The operation interface 1214 is connected with an operation unit such as a mouse device 1211, a keyboard 1210 or a touch panel device. The computer 1200' may include two or more of each component. Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', etc.

A computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 1200, 1200', communicates with the PIU 110, the rotary junction (e.g., the RJ, etc.), the motor PM, the motor SM, the catheter 120 and/or one or more other components of a system, such as the system 100, 100', 100", 100''', etc., to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate a system (e.g., the system 100, the system 100', the system 100", the system 100''', etc.), for example when performing OCT or other imaging technique, including, but not limited to, detection of lumen edge(s) and/or artifact(s), and/or detecting and guiding optical connections. An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100', the system 100", the system 100''', the systems/apparatuses of FIGS. 3A-3J, etc.) to set or change the imaging condition, and to start or end the imaging, and/or to start or end the lumen detection, stent(s) detection, artifact(s) detection, and/or detection and guidance of optical connection(s). The laser source 101 of an OCT system as aforementioned may have interfaces to communicate with the computers 1200, 1200' to send and receive the status information and the control signals.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 7,872,759; 8,289,522; and 8,928,889 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942 and U.S. Patent Publication Nos. 2010/0092389, 2012/0101374, 2016/0228097, 2018/0045501 and 2018/0003481, each of which patents, patent publications and patent application(s) are incorporated by reference herein in their entireties. As aforementioned, any feature or aspect of the present disclosure may be used with OCT imaging systems, apparatuses, methods, storage mediums or other aspects or features as discussed in U.S. patent application Ser. No. 16/414,222, filed on May 16, 2019, the entire disclosure of which is incorporated by reference herein in its entirety, as discussed in U.S. Pat. Pub. No. 2019/0374109, which was published on Dec. 12, 2019, the disclosure of which is incorporated by reference herein in its entirety, as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications, equivalent structures and functions.

The invention claimed is:

1. A system for increasing imaging depth range, comprising:
   an imaging apparatus or system using one or more imaging modalities;
   a reference reflection adjusted so that a reflection from a system mating connector is visible in an imaging field of view; and
   one or more processors that operate to determine if a probe or catheter is mated to the system mating connector by measuring signal-to-noise ratio (SNR) or a peak in at least one A-line scan of the system mating connector and by determining that, in a case where the peak in the at least one A-line scan of the system mating connector is measured, the peak is present at or about the system mating connector.

2. An apparatus for detecting and guiding one or more optical connections for one or more imaging modalities, the apparatus comprising:
   one or more processors that operate to:
   switch the apparatus from a main reference arm to an auxiliary reference arm;
   move a linear stage and a rotary motor of the apparatus to pre-engagement or pre-disengagement positions;
   measure a, or use a previously stored, signal-to-noise ratio (SNR) or a peak in at least one A-line scan of a patient interface component (PIC) output connector prior to engagement or disengagement of the one or more optical connections between the PIC and a catheter or probe;
   move the linear stage of the apparatus to an engagement position or to a post-disengagement position;
   measure an SNR or a peak of the PIC output connector after the engagement and/or the disengagement; and
   determine that (i) in a case where the engagement occurs, the engagement is successful or acceptable in a case where a post-engagement SNR or peak is different from the pre-engagement SNR or peak, and/or in a case where the apparatus confirms, or the one or more processors of the apparatus confirm, that only one peak is present in at least one A-line at or about the PIC output connector; and/or (ii) in a case where the disengagement occurs, that the disengagement is successful or acceptable in a case where a post-disengagement SNR or peak is different from the pre-disengagement SNR or peak, and/or in a case where the apparatus confirms, or the one or more processors of the apparatus confirm, that a second peak is present in at least one A-line at a distance from the PIC output connector about equal or equal to a distance between pre-disengagement and post-disengagement positions or about where the catheter or probe connector is expected or estimated.

3. The apparatus of claim 2, wherein the one or more processors further operate to use crosstalk noise as a metric for detecting and guiding the one or more optical connections.

4. The apparatus of claim 2, wherein the one or more processors further operate to use data from measured peak and noise levels of the at least one A-line or of several A-lines.

5. The apparatus of claim 2, wherein the one or more processors further operate to control one or more of the following: (i) a mechanical mating of a sacrificial interface of the apparatus to a connector of the catheter or probe; and/or (ii) a mechanical de-mating of a sacrificial interface of the apparatus from a connector of the catheter or probe.

6. The apparatus of claim 2, wherein the one or more processors further operate to move the linear stage and rotary motor to pre-engagement positions and measure or use a previously stored, unmated PIC output connector SNR or pre-engage SNR.

7. The apparatus of claim 2, wherein the one or more processors further operate to, in the case where the apparatus or the one or more processors confirm that only one peak is present, confirm that the only one peak is present in the at least one A-line at or about where the PIC output connector peak is expected or estimated.

8. The apparatus of claim 2, wherein the apparatus further comprises or is connected to one or more of the following:
a light source that operates to produce a light;
an interference optical system that operates to: (i) receive and divide the light from the light source into a first light with which an object or sample is to be irradiated and a second reference light, (ii) send the second reference light for reflection off of a reference mirror of the interference optical system, and (iii) generate interference light by causing reflected or scattered light of the first light with which the object or sample has been irradiated and the reflected second reference light to combine or recombine, and to interfere, with each other, the interference light generating one or more interference patterns; and/or
one or more detectors that operate to continuously acquire the interference light and/or the one or more interference patterns such that the at least one A-line or A-lines is/are obtained.

9. The apparatus of claim 2, wherein the one or more imaging modalities includes one or more of the following: Optical Coherence Tomography (OCT), intravascular ultrasound (IVUS), another lumen image(s) modality, and an intravascular imaging modality.

10. An apparatus for detecting and guiding one or more optical connections for one or more imaging modalities, the apparatus comprising:

one or more processors that operate to:
switch the apparatus from a main reference arm to an auxiliary reference arm;
move a linear stage and a rotary motor of the apparatus to pre-engagement and/or pre-disengagement positions;
move the linear stage to one of the following: (i) an engagement position for engagement of the one or more optical connections between a patient interface component (PIC) and a catheter or probe while measuring a distance between a reflection of a PIC output connector and a reflection of a catheter or probe connector; and/or (ii) a post-disengagement position for disengagement between the one or more optical connections between a patient interface component (PIC) and a catheter or probe while measuring a distance between a reflection of a PIC output connector and a reflection of a catheter or probe connector;
use the distance information to guide and determine when the engagement position or the post-disengagement position is reached;
perform a pullback of the linear stage to release mechanical tension and to determine a status of one or more optical connections of the apparatus in a case where the engagement position is reached; and
determine that (i) in a case where the engagement occurs, the engagement is successful or acceptable in a case where only one peak is present in at least one A-line scan of, or at or about, the PIC output connector and/or (ii) in a case where the disengagement occurs, the disengagement is successful or acceptable in a case where there is more than one peak present in at least one A-line scan where the peaks are separated by a distance consistent with a mechanical distance traveled by the linear stage within a margin of error or by a determined distance within a margin of error.

11. The apparatus of claim 10, wherein the apparatus further comprises or is connected to one or more of the following:
a light source that operates to produce a light;
an interference optical system that operates to: (i) receive and divide the light from the light source into a first light with which an object or sample is to be irradiated and a second reference light, (ii) send the second reference light for reflection off of a reference mirror of the interference optical system, and (iii) generate interference light by causing reflected or scattered light of the first light with which the object or sample has been irradiated and the reflected second reference light to combine or recombine, and to interfere, with each other, the interference light generating one or more interference patterns; and/or
one or more detectors that operate to continuously acquire the interference light and/or the one or more interference patterns such that the at least one A-line or A-lines is/are obtained.

12. The apparatus of claim 10, wherein the one or more imaging modalities includes one or more of the following: Optical Coherence Tomography (OCT), intravascular ultrasound (IVUS), another lumen image(s) modality, and an intravascular imaging modality.

13. A method for detecting and guiding one or more optical connections for one or more imaging modalities of an apparatus or system, the method comprising:
switching the apparatus or system from a main reference arm to an auxiliary reference arm;
moving a linear stage and a rotary motor of the apparatus or system to pre-engagement and/or pre-disengagement positions;

measuring a, or use a previously stored, signal-to-noise ratio (SNR) or a peak in at least one A-line scan of a patient interface component (PIC) output connector prior to engagement or disengagement of the one or more optical connections between the PIC and a catheter or probe;

moving the linear stage of the apparatus or system to an engagement position and/or to a post-disengagement position;

measuring an SNR or a peak of the PIC output connector after the engagement and/or the disengagement; and determining that (i) in a case where the engagement occurs, the engagement is successful or acceptable in a case where a post-engagement SNR or peak is different from the pre-engagement SNR or peak, and/or in a case where the apparatus or system confirms, or the apparatus or system confirms, that only one peak is present in at least one A-line at or about the PIC output connector, and/or (ii) in a case where the disengagement occurs, the disengagement is successful or acceptable in a case where a post-disengagement SNR or peak is different from the pre-disengagement SNR or peak, and/or in a case where the apparatus or system confirms that a second peak is present in at least one A-line at a distance from the PIC output connector about equal or equal to a distance between pre-disengagement and post-disengagement positions or about where the catheter or probe connector is expected or estimated.

14. A method for detecting and guiding one or more optical connections for one or more imaging modalities of an apparatus or system, the method comprising:

switching the apparatus or system from a main reference arm to an auxiliary reference arm;

moving a linear stage and a rotary motor of the apparatus or system to pre-engagement and/or pre-disengagement positions;

moving the linear stage to an engagement position for engagement of the one or more optical connections between a patient interface component (PIC) and a catheter or probe while measuring a distance between a reflection of a PIC output connector and a reflection of a catheter or probe connector, or moving the apparatus to a post-disengagement position for disengagement between the one or more optical connections between a patient interface component (PIC) and a catheter or probe while measuring a distance between a reflection of a PIC output connector and a reflection of a catheter or probe connector;

using the distance information to guide and determine when the engagement position or the post-disengagement position is reached;

performing a pullback of the linear stage to release mechanical tension and to determine a status of one or more optical connections of the apparatus or system in a case where the engagement position is reached; and determining that (i) in a case where the engagement occurs, the engagement is successful or acceptable in a case where only one peak is present in at least one A-line scan of, or at or about, the PIC output connector and/or (ii) in a case where the disengagement occurs, the disengagement is successful or acceptable in a case where there is more than one peak present in at least one A-line scan where the peaks are separated by a distance consistent with a mechanical distance traveled by the linear stage within a margin of error or by a determined distance within a margin of error.

15. The apparatus of claim 10, wherein the one or more processors further operate to, in a case where the one or more processors determine that the engagement is not successful or acceptable, repeat the switch, move a linear stage and a rotary motor, move the linear stage to an engagement position, use the distance information, perform a pullback of the linear stage, and determine that the engagement is successful or acceptable attributes of the one or more processors.

16. The method of claim 14, wherein the method further comprises, in a case where it is determined that the engagement is not successful or acceptable, repeating the switching, moving a linear stage and a rotary motor, moving the linear stage to an engagement position, using the distance information, performing a pullback of the linear stage, and determining that the engagement is successful or acceptable steps.

* * * * *